US009622734B2

(12) United States Patent
Ryshkus et al.

(10) Patent No.: US 9,622,734 B2
(45) Date of Patent: Apr. 18, 2017

(54) RETRACTOR TOOLS FOR MINIMALLY INVASIVE HIP SURGERY

(71) Applicant: Greatbatch Ltd., Clarence, NY (US)

(72) Inventors: Chad E. Ryshkus, Kansasville, WI (US); Douglas J. Roger, Rancho Mirage, CA (US); Jonathan P. Crandall, Fort Wayne, IN (US)

(73) Assignee: Greabatch Ltd., Clarence, NY (US)

( * ) Notice: Subject to any disclaimer, the term of this patent is extended or adjusted under 35 U.S.C. 154(b) by 0 days.

(21) Appl. No.: 14/662,536

(22) Filed: Mar. 19, 2015

(65) Prior Publication Data
US 2015/0196289 A1 Jul. 16, 2015

Related U.S. Application Data

(63) Continuation of application No. 13/194,176, filed on Jul. 29, 2011, now abandoned.

(51) Int. Cl.
*A61B 17/02* (2006.01)
*A61B 17/00* (2006.01)

(52) U.S. Cl.
CPC ........ *A61B 17/025* (2013.01); *A61B 17/0218* (2013.01); *A61B 2017/0088* (2013.01); *A61B 2017/0275* (2013.01)

(58) Field of Classification Search
CPC .................. A61B 17/02; A61B 17/025; A61B 2017/0268; A61B 2017/0275; A61B 17/0218

(Continued)

(56) References Cited

U.S. PATENT DOCUMENTS 1,497,749 A * 6/1924 Diack ........................... 433/144
2,666,428 A * 1/1954 Glenner ........................ 600/210
(Continued)

FOREIGN PATENT DOCUMENTS

| CN | 201356580 | 12/2009 |
| EP | 0986329 | 11/2009 |
| JP | 2003310624 | 11/2003 |

OTHER PUBLICATIONS

Omni-Tract Surgical. "Omni-Flex™ Pediatric Retractor System." Pediatric Surgery—Product Facts 2006. Web. <http://www.integralife.com/products%2Fpdfs%2Fomni-flex%20po100%20%2840-6164%29_591.pdf> accessed May 28, 2015.*

(Continued)

*Primary Examiner* — Todd E Manahan
*Assistant Examiner* — Marcela I Shirsat
(74) *Attorney, Agent, or Firm* — Michael F. Scalise

(57) ABSTRACT

A retractor system, kit and method of use includes a plurality of retractors for use in retracting a wound during a minimally-invasive hip replacement surgery to define an access space to a surgical site is discussed. Each of the retractors comprises a handle portion configured to be held by a user, a curved bend portion distal of the handle portion, and a wound contact portion attached to the curved bend portion. The wound contact portion is configured to contact tissue of the wound when at least a portion of the retractor is inserted through a skin incision that defines the wound. Each retractor also has a distal portion disposed distally of the wound contact portion, wherein the wound contact portion has a generally curved cross-sectional profile perpendicular to its length that is configured to prevent necrosis of the tissue during retraction. In addition, the cross-sectional profile provides an improved line of sight during the surgical procedure. Furthermore, the cross-sectional profile prevents (Continued)

the jamming of a cutting device, such as a reamer inserted through the incision, while the retractors retract the wound.

27 Claims, 21 Drawing Sheets

(58) Field of Classification Search
USPC ....... 600/201, 204, 210, 214, 217, 226–228, 600/230, 235; 606/81, 89, 91; 623/22.12
See application file for complete search history.

(56) References Cited

U.S. PATENT DOCUMENTS

| | | | |
|---|---|---|---|
| 2,695,607 A * | 11/1954 | Hipps et al. | 600/210 |
| 3,381,685 A | 5/1968 | Solbrig | |
| 3,955,568 A | 5/1976 | Neufeld | |
| D275,227 S | 8/1984 | Garner | |
| 4,610,243 A * | 9/1986 | Ray | 600/206 |
| 4,642,121 A | 2/1987 | Keller | |
| 4,934,352 A | 6/1990 | Sullivan | |
| 4,995,875 A | 2/1991 | Coes | |
| D318,116 S | 7/1991 | Michelson | |
| 5,217,463 A | 6/1993 | Mikhail | |
| 5,290,290 A | 3/1994 | Mikhail | |
| 5,303,694 A | 4/1994 | Mikhail | |
| 5,351,680 A | 10/1994 | Jung | |
| 5,514,077 A * | 5/1996 | Rabban | 600/226 |
| D393,318 S | 4/1998 | Wolter | |
| 5,743,853 A | 4/1998 | Lauderdale | |
| D395,510 S | 6/1998 | Furnish | |
| 5,891,147 A * | 4/1999 | Moskovitz | A61B 17/02 606/79 |
| D442,687 S | 5/2001 | Schulz | |
| D449,689 S | 10/2001 | Comeau et al. | |
| 6,315,718 B1 | 11/2001 | Sharratt | |
| 6,428,472 B1 | 8/2002 | Haas | |
| 6,679,888 B2 | 1/2004 | Green et al. | |
| 6,855,149 B2 | 2/2005 | Dye | |
| 6,926,728 B2 | 8/2005 | Zucherman et al. | |
| D522,140 S | 5/2006 | Stalcup et al. | |
| D523,142 S | 6/2006 | Stalcup et al. | |
| D531,310 S | 10/2006 | Wolter et al. | |
| 7,214,186 B2 | 5/2007 | Ritland | |
| 7,300,400 B2 | 11/2007 | Brown | |
| D568,471 S | 5/2008 | Engler | |
| 7,468,077 B2 | 12/2008 | Rochetin | |
| D589,145 S | 3/2009 | Miller | |
| D628,291 S | 11/2010 | Palmer et al. | |
| D629,896 S | 12/2010 | Horton | |
| 7,909,848 B2 | 3/2011 | Patel et al. | |
| 2004/0172038 A1 * | 9/2004 | Dye | 606/91 |
| 2005/0059978 A1 | 3/2005 | Sherry et al. | |
| 2005/0182301 A1 | 8/2005 | Acker et al. | |
| 2007/0021655 A1 | 1/2007 | Sayeg et al. | |
| 2007/0060795 A1 | 3/2007 | Vayser et al. | |
| 2007/0066872 A1 | 3/2007 | Morrison et al. | |
| 2007/0208226 A1 | 9/2007 | Grey et al. | |
| 2008/0228191 A1 * | 9/2008 | Downs | A61B 17/025 606/90 |
| 2009/0012370 A1 | 1/2009 | Gutierrez et al. | |
| 2009/0216089 A1 * | 8/2009 | Davidson | A61B 17/02 600/235 |
| 2009/0299147 A1 | 12/2009 | Epstein et al. | |
| 2014/0128684 A1 * | 5/2014 | Carlson | 600/217 |

OTHER PUBLICATIONS

Innomed, "Bent Hohmann Retractors—Narrow".
Innomed, "Cobra Retractors".
Innomed, "Minimally Invasive Hip Surgery Retractors".
Innomed, "Mueller-type Femoral Neck Retractor and Lester Medial Femoral Neck Retractor".

* cited by examiner

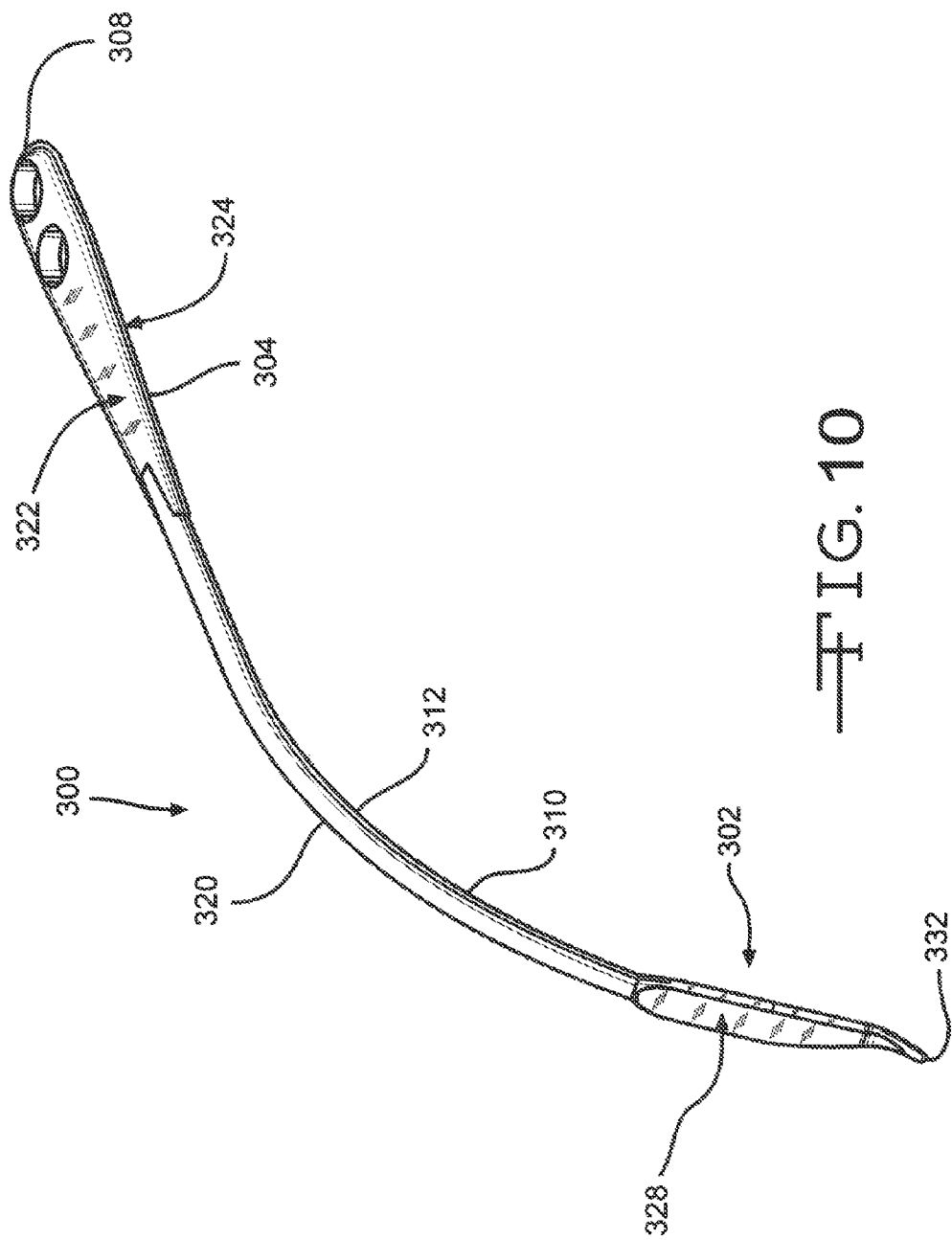

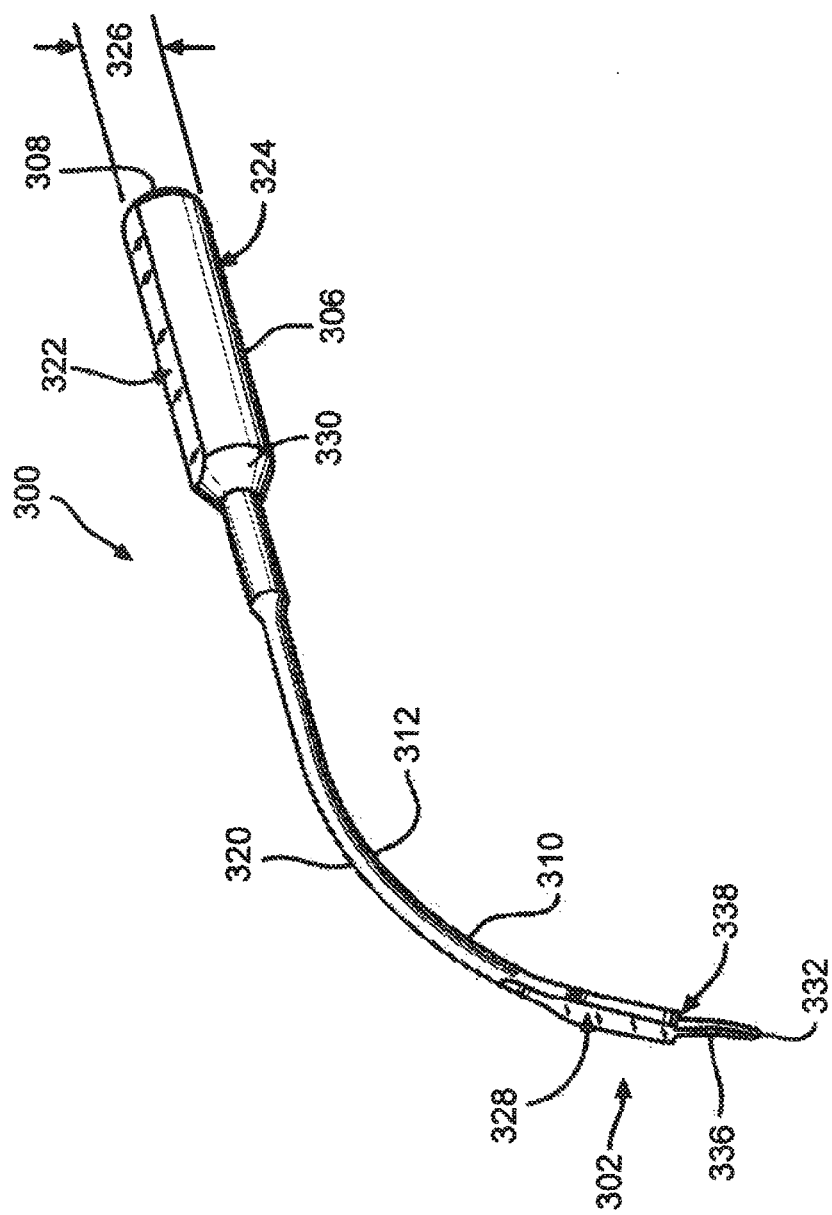

RETRACTOR TOOLS FOR MINIMALLY INVASIVE HIP SURGERY

CROSS-REFERENCE TO RELATED APPLICATIONS

This application is a continuation of U.S. patent application Ser. No. 13/194,176, filed on Jul. 29, 2011, now abandoned, which claims priority from U.S. Pro. Pat. App. Ser. Nos. 61/368,754, filed Jul. 29, 2010; 61/368,761, filed Jul. 29, 2010; and 61/368,768 filed Jul. 29, 2010.

1. FIELD OF THE INVENTION

The present invention is directed to minimally invasive surgery, and more particularly to retractor tools for use in minimally invasive hip replacement surgery.

2. PRIOR ART

Approximately 200,000 hip replacements are performed each year in the United States and the number is expected to continue to grow as the population continues to age. The usual reasons for hip replacement are osteoarthritis, rheumatoid arthritis and traumatic arthritis, all of which can cause pain and stiffness that limit mobility and the ability to perform daily living activities. Hip replacement surgery is usually performed where other measures (e.g. physical therapy, medications, and walking aids) are unable to overcome the chronic pain and disability associated with these conditions.

Various techniques are used by orthopedic surgeons to perform hip replacements. These include the following approaches: anterior, antero-lateral, lateral, postero-lateral and posterior. The posterior and postero-lateral approaches account for approximately 60%-70% of hip replacement surgeries.

Traditional hip replacement surgery involves an open surgical procedure and extensive surgical dissection. However, such procedures require a longer recovery period and rehabilitation time for the patient. The average hospital stay for open hip replacement procedures is 4-5 days, followed in most cases by extensive rehabilitation.

More recently, there has been considerable interest and research done in Minimally Invasive Surgery (MIS), including the use of MIS procedures in connection with hip replacement surgery. In comparison with the traditional open surgical approach, MIS hip replacement surgeries involve fewer traumas to the muscles surrounding the hip joint. Specifically, fewer muscles that help to stabilize the hip joint are cut in MIS hip replacement surgeries, reducing the risk of dislocation of the hip surgery and speeding recovery. Patients spend less time in the hospital and return to normal life activities more quickly.

MIS approaches use smaller surgical openings, which require specialized instruments to perform hip replacement procedures. Some of these instruments are surgical retractors used to retract tissue. This allows visualization of the surgical site and insertion of surgical tools, such as reamers, broaches and ultimately surgical implants. However, the use of conventional retractors in MIS hip surgery has often resulted in necrosis of the tissue that borders the incision and against which the retractors are pressed to maintain the access path to the surgical site. This necrosis can necessitate the surgical excision of such tissue. Additionally, conventional hip surgery retractors have a flat and generally rectangular cross-sectional profile. This frequently results in impingement on the rotating reamer as the latter is inserted through the incision to ream the acetabulum. Accordingly, there is a need for an improved retractor tool for use in MIS orthopedic procedures (e.g., hip replacement surgery) that addresses some of the shortcomings in the existing surgical retractors noted above.

SUMMARY OF THE INVENTION

In accordance with one embodiment, a retractor for use in minimally invasive hip replacement surgery is provided. The retractor comprises a handle portion configured to be held by a user and a curved bend portion distal to the handle portion. A wound contact portion is attached to the curved bend portion, the wound contact portion configured to contact tissue of a wound when at least a portion of the retractor is inserted through a skin incision that defines the wound. In addition, a distal portion disposed distally of the wound contact portion, contacts the bony anatomy, particularly of the acetabulum and proximal femur. The wound contact portion has a generally curved cross-sectional profile perpendicular to its length that is configured to prevent necrosis of wound tissue during retraction of the wound with the retractor.

In accordance with another embodiment, a retractor with an alternate design for use in minimally invasive hip replacement surgery is provided. This alternate retractor embodiment comprises a handle portion, configured to be held by a user that is centrally located between two wound contact portions. Two distal wound contact portions extend distally from the centrally located handle portion. The wound contact portions are configured to contact tissue of a wound when at least a portion of the retractor is inserted through a skin incision that defines the wound.

Both retractor embodiments comprise a shaft that connects the handle portion to the wound contact portion and distal portion of the retractor. In addition to reducing tissue necrosis, the curved cross-sectional profile of the shaft provides an improved line of site during surgical procedures. The curved cross-sectional profile of the shaft minimizes visual obstruction thereby resulting in improved control of the tool during the surgical procedure.

BRIEF DESCRIPTION OF THE DRAWINGS

FIG. 4A is a cross-sectional view of a shaft of the piriformis retractor embodiment shown in FIG. 4.

FIG. 7A is a cross-sectional view of a shaft of the posterior acetabular retractor embodiment shown in FIG.

FIG. 10 illustrates a perspective view of an embodiment of an anterior retractor.

FIG. 10B shows a perspective view of an alternate embodiment of an anterior retractor.

FIG. 13A shows a cross-sectional view of a shaft of the femoral neck retractor embodiment shown in FIG. 13.

FIG. 16A shows a cross-sectional view of a shaft of the double ended retractor embodiment shown in FIG. 16.

DETAILED DESCRIPTION OF THE PREFERRED EMBODIMENTS

Figure 1:
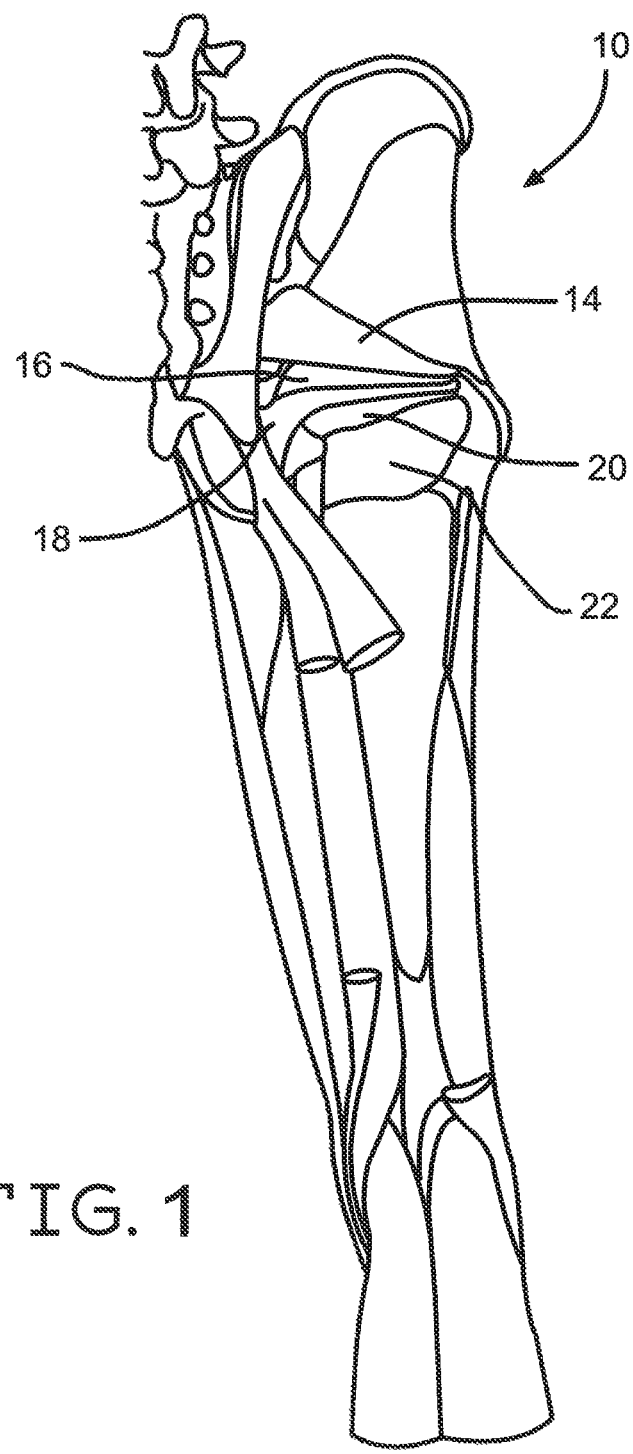
FIG. 1 is a schematic drawing illustrating an anatomical region of the hip area.
Figure 2:
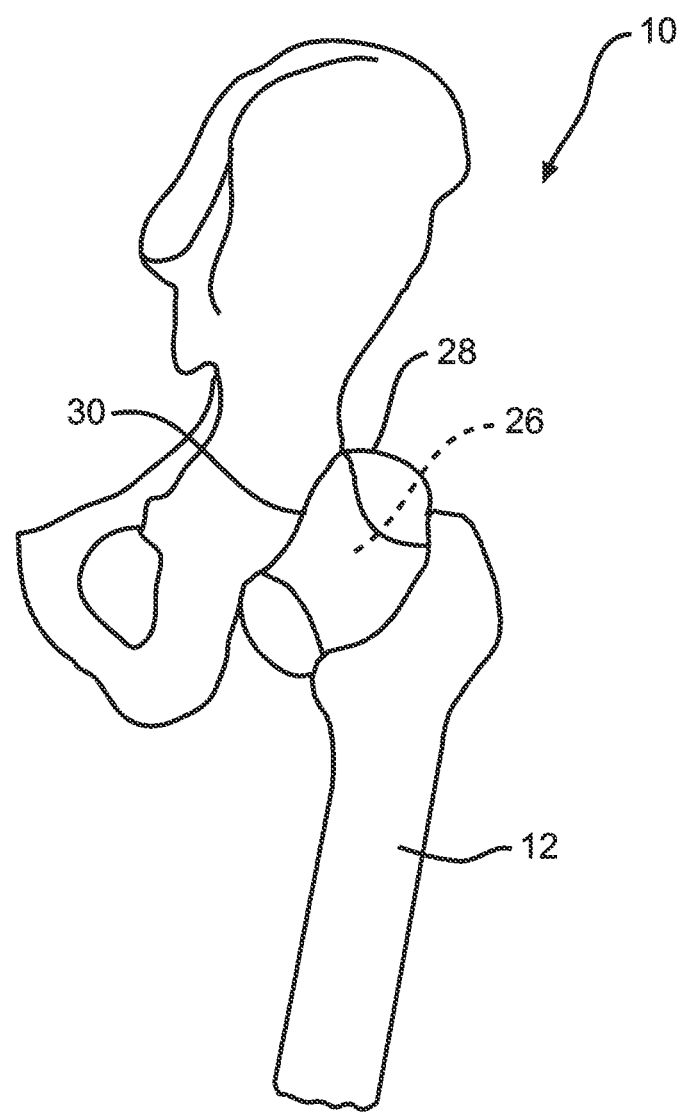
FIG. 2 is a schematic drawing of an area of the pelvic region of a human.
Figure 3:
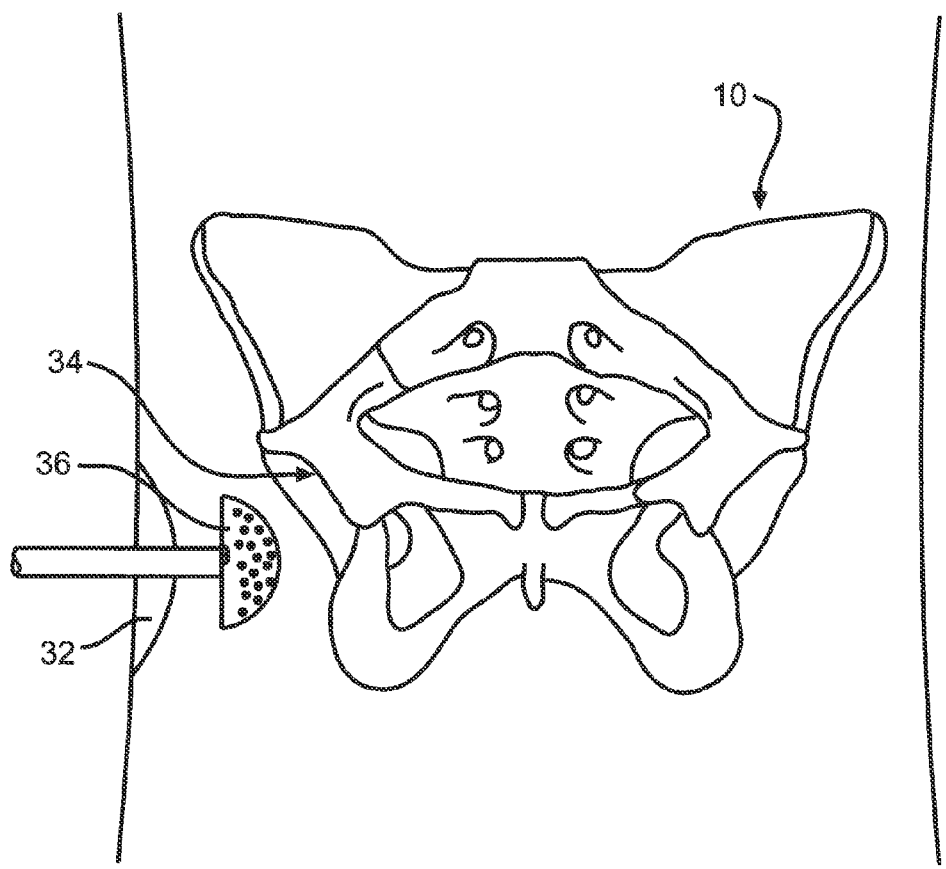
FIG. 3 is a schematic drawing of a pelvic girdle of a human.

Now turning to the figures, FIGS. 1-3 illustrate some features of the musculoskeletal anatomy, specifically the hip region 10 of a human. FIGS. 4-18 illustrate embodiments of orthopedic retractor tools of the present invention. As shown in FIGS. 1-3, there are several muscles that act to stabilize the femoral head of a femur bone 12 in the acetabulum (FIG. 2). These muscles include the short external rotator muscles (i.e., the piriformis 14, the superior gemellus 16, the obturator internus 18, the inferior gemellus 20, the obturator externus (not shown) and the quadratus femoris 22). The gluteus maximus (not shown) extends over these short external rotator muscles. The femoral head 26 is enclosed in a fibrous capsule 28, which attaches to the hip bone outside the acetabular lip 30 and to the base of the neck of the femoral head 26.

The MIS posterior hip replacement approach has traditionally involved first a skin incision, followed by an incision in the fascia lata, and then detachment of the short external rotator muscles of the hip 10. However, it has been found that through a modified MIS posterior hip replacement approach only the piriformis muscle 14, and occasionally the superior gemellus 16, requires detachment. Through this modified MIS approach, the obturator internus 18, inferior gemellus 20, the obturator externus (not shown) and the quadratus femoris 22 are always left intact.

In a preferred embodiment, the surgeon begins by making an incision 32 in a posterior side of a patient's hip 10 (e.g., on the buttocks) on a side proximate the hip joint to be treated. The surgeon can then separate fibers in the gluteus maximus longitudinally (not cut transversely) using a transgluteus maximus approach to access the external rotators of the hip 10 and then the hip capsule 28. The present approach does not involve an incision in the fascia lata, which is required in other posterior surgical approaches, as well as in the antero-lateral and lateral approaches to the hip 10. The surgeon can then detach the pirifromis 14, and sometimes the superior gemellus 16, which, as discussed above, are the only short external rotator muscles that are detached with this approach. This approach preserves the obturator internus 18, inferior gemellus 20, obturator externus (not shown) and quadratus femoris 22, which provides significant additional stability to the hip 10, and contributes to a faster post operative recovery.

Once access to the acetabulum 34 is achieved, the surgeon can advance a cutting tool 36 such as a reamer, through the wound defined by the incision 32 to the surgical site proximate the acetabulum 34 and prepare the bone for implantation of a prosthetic cup (not shown). In an embodiment, the femoral head 26 is also removed and a prosthetic hip stem (not shown) is implanted into the femur 12, the prosthetic hip stem comprises a modular femoral head that articulates with the acetabular cup prosthesis. Once the prosthesis is in place, the capsule 28 can be closed, followed by closure of the incision 32.

FIGS. 4, 4A, 5 and 6 show a preferred embodiment of a retractor 100, namely, a piriformis retractor which is also generally referred to as an inferior acetabular retractor. The retractor 100 has a handle portion 102, a bend portion 104, a wound contact portion 106 and a distal portion 108. As shown, the distal portion 108 can have a generally rectangular cross-section. Although a rectangular cross-section is preferred, the distal portion 108 may have a curved cross-section. In a preferred embodiment, a length 112 of the retractor 100 extends from a proximal end 110 to the wound contact portion 106. It is preferred that the length 112 ranges from about 200 mm to about 400 mm. Furthermore, a shaft 114 extends therebetween the wound contact portion 106 and the handle portion 102.

The shaft 114 preferably has a curved cross-sectional profile perpendicular to its length, and more preferably a round cross-sectional profile as shown in FIG. 4A. In a preferred embodiment, the shaft 114 has a thickness 116 that ranges from about 5 mm to about 10 mm in diameter. However, it is contemplated that the thickness 116 of the shaft 114 may be larger than 10 mm or smaller than 5 mm.

Figure 5:
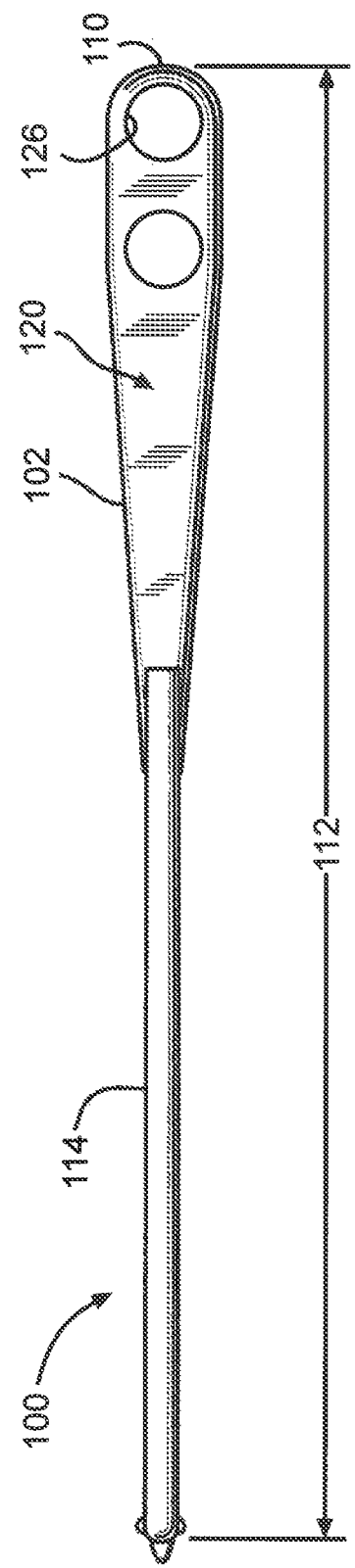
FIG. 5 shows a top view of the piriformis retractor embodiment shown in FIG. 4.

The bend portion 104 resides therebetween the handle portion 102 and the distal portion 108 of the retractor 100 as shown in FIG. 5. The bend portion 104 has a bend angle 118 that generally measures about 90°. The bend angle 118 is measured between horizontal axis A-A, co-axial to the handle portion 102, and perpendicular axis E-B. Alternatively, bend portion 104 may have a bend angle 118 that ranges from about 70° to about 130°.

The handle portion 102 resides at the proximal end 110 of the retractor 100. In a preferred embodiment, the handle portion 102 has a rectangular cross-section with a generally planar top 120 and bottom surface 122. Alternatively, the handle portion 102 may be constructed with a round or oval cross-section. The handle 102 can have a thickness 124 that may be larger or smaller than the thickness 116 of the shaft 114. An opening 126 may extend through the handle portion 102 from the top surface 120 through the bottom surface 122.

The distal portion 108 of the retractor 100 preferably has a height 128 ranging from about 50 mm to about 100 mm, a thickness 130 of about 3 mm and a maximum width 134 of about 12 mm. Furthermore, a height 132 extends between the distal end 138 of the retractor 100 and a bottom surface 122 of the handle portion. It is preferred that this height 132 range from about 100 mm to about 200 mm.

Figure 4:
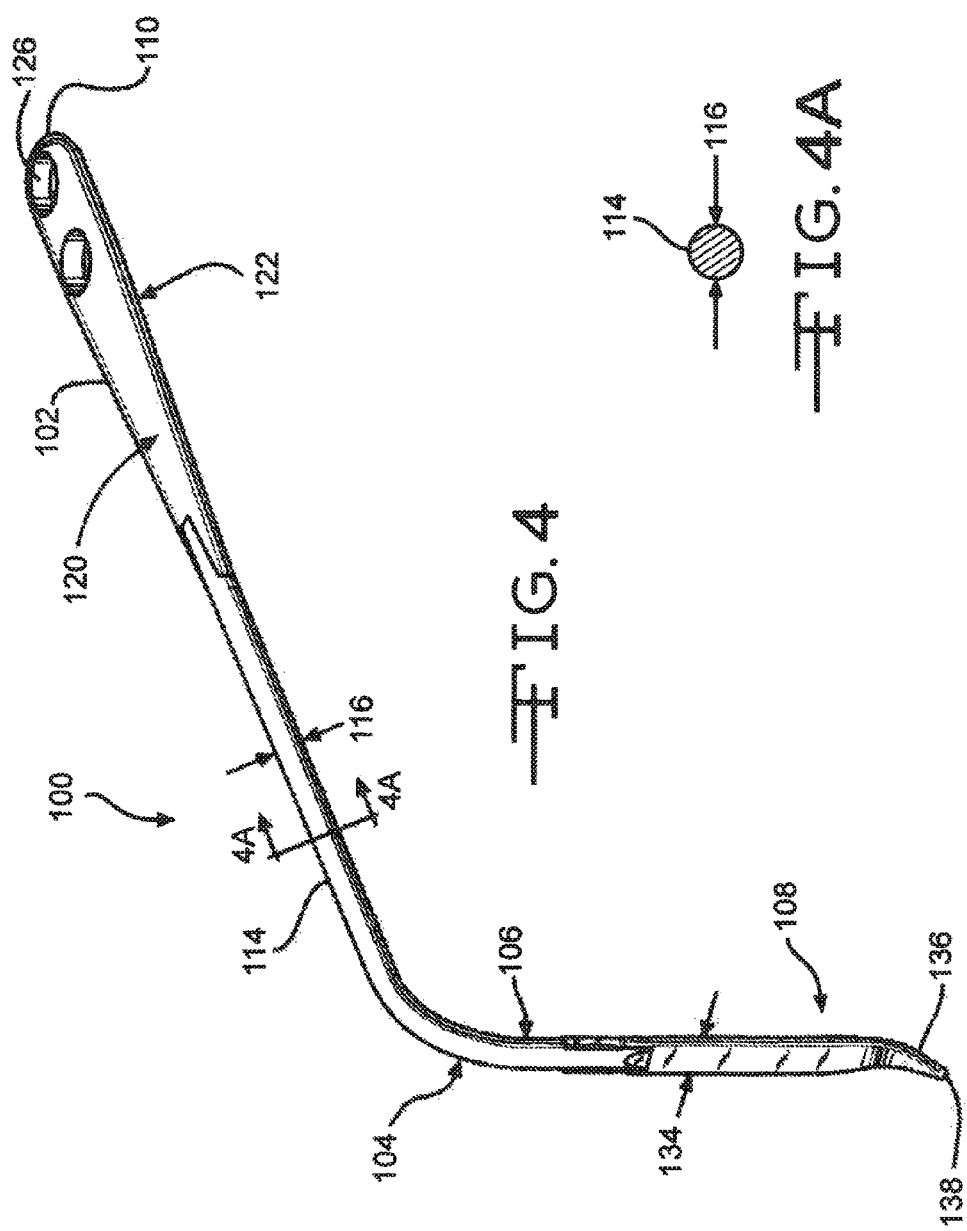
FIG. 4 is a perspective view illustrating an embodiment of a piriformis retractor.
Figure 6:
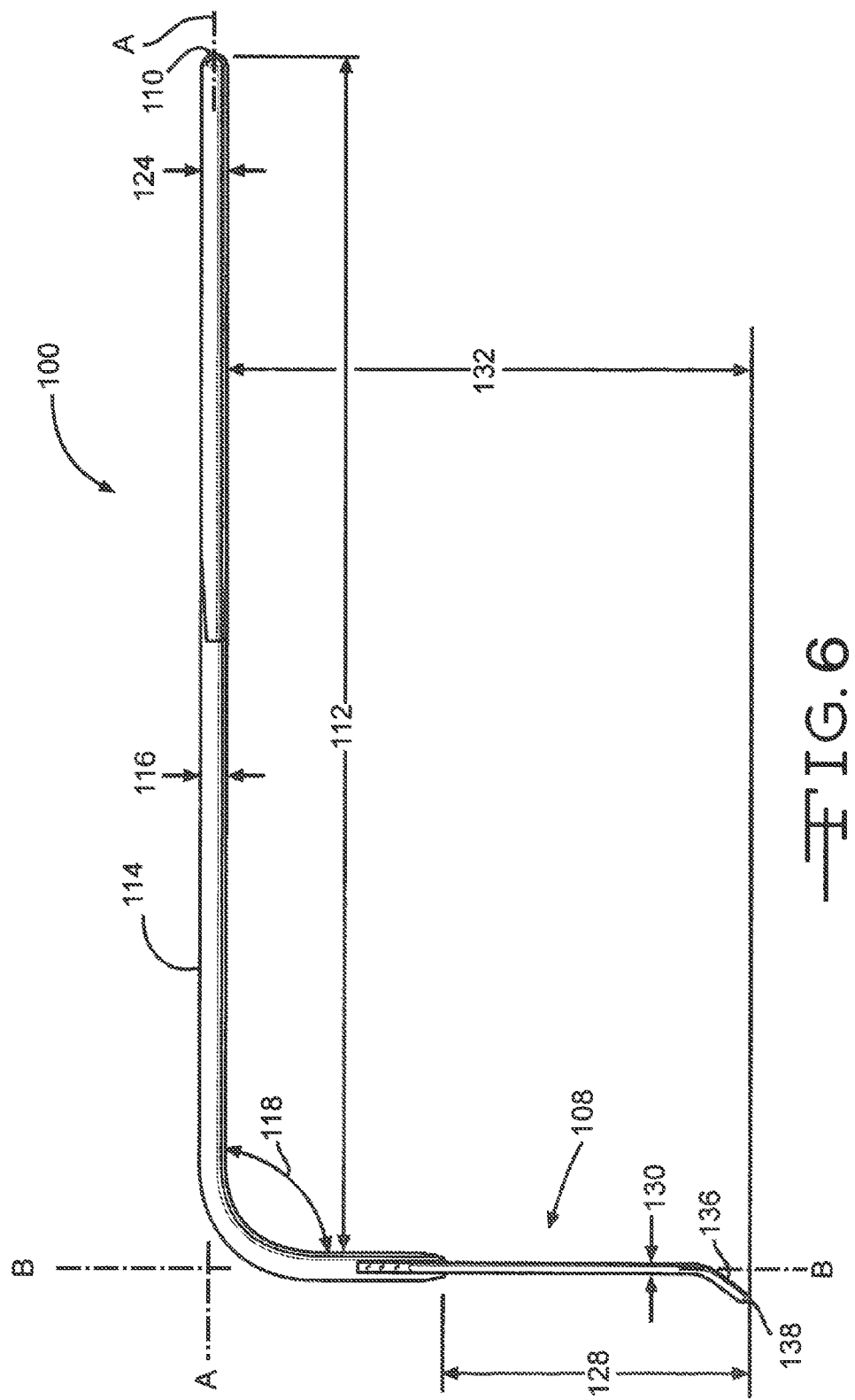
FIG. 6 illustrates a side view of the piriformis retractor embodiment shown in FIG. 4.

In a preferred embodiment, the distal portion 108 has a generally rectangular cross-section with a distal portion width 134 that may range from about 2 mm to about 20 mm. In a preferred embodiment, the width 134 of the distal portion 108 gradually decreases to a pointed end. As illustrated, a prong 136 extends to the distal end 138 of the retractor 100. The prong 136 preferably bends in an upwardly and outwardly direction from perpendicular axis B-B as shown in FIGS. 4 and 6. In a preferred embodiment, prong 136 bends outwardly or inwardly about 1° to about 15° from perpendicular axis B-B. However, it is contemplated that the retractor 100 may be constructed with other dimensions that are larger or smaller than those given above.

FIGS. 7, 7A, 8 and 9 illustrate a preferred embodiment of a retractor 200 generally referred to as a "posterior acetabular retractor". As illustrated, the retractor 200 generally comprises an "S" shaped curve portion 202 distal of its handle portion 204. The MS" shaped curve portion 202 comprises a first bend portion 206 and a second bend portion 208. As illustrated, the retractor 200 further comprises a wound contact portion 210 and a distal portion 212. A shaft 214 extends distally from the handle portion 204 to a distal end 216 of the retractor 200.

In an embodiment, a length 218 of the retractor 200 extends from the proximal end 220 to the wound contact portion 210. In a preferred embodiment, the length 218 ranges from about 300 mm to about 400 mm. A thickness 222 of the shaft 214 has a diameter that ranges between about 5 mm to about 10 mm.

Similar to retractor 100 as previously discussed, the handle portion 204 of retractor 200 resides at the proximal end 220 of the retractor 200. Like retractor 100, the handle portion 204 has a generally rectangular cross-section with a generally planar top 224 and bottom surface 226. Alternatively, the handle portion 204 may be constructed with a round or oval cross-section. The handle portion 204 can have a handle thickness 228 that may be larger or smaller than the thickness 222 of the shaft 214. An opening 230 may extend through the handle portion 204 extending from the top surface 224 through the bottom surface 226.

The first bend portion 206 has a first radius of curvature 232. The first radius of curvature 232 is defined by the radius that resides along a surface 234 of the first bend portion 206 that extends from a horizontal axis CC of the handle portion 204 to an apex point 236, positioned between the first and second bend portions 206, 208. The first bend portion 206 generally has a curved cross sectional profile perpendicular to its length, and more preferably, a round cross-sectional profile. It is preferred that the first radius of curvature 232 ranges from about 5 mm to about 25 mm.

Figure 7:
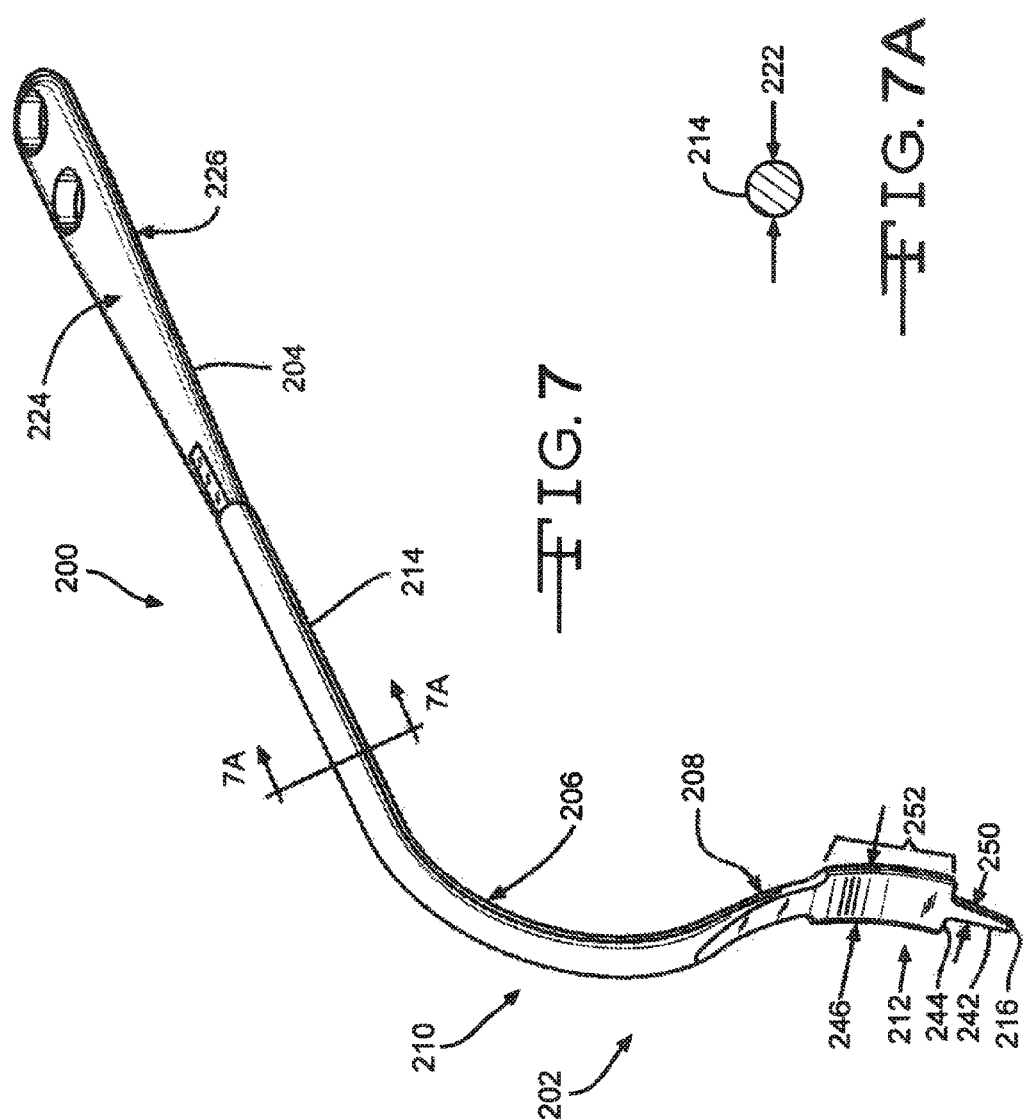
FIG. 7 is a perspective view of an embodiment of a posterior acetabular retractor.
Figure 8:
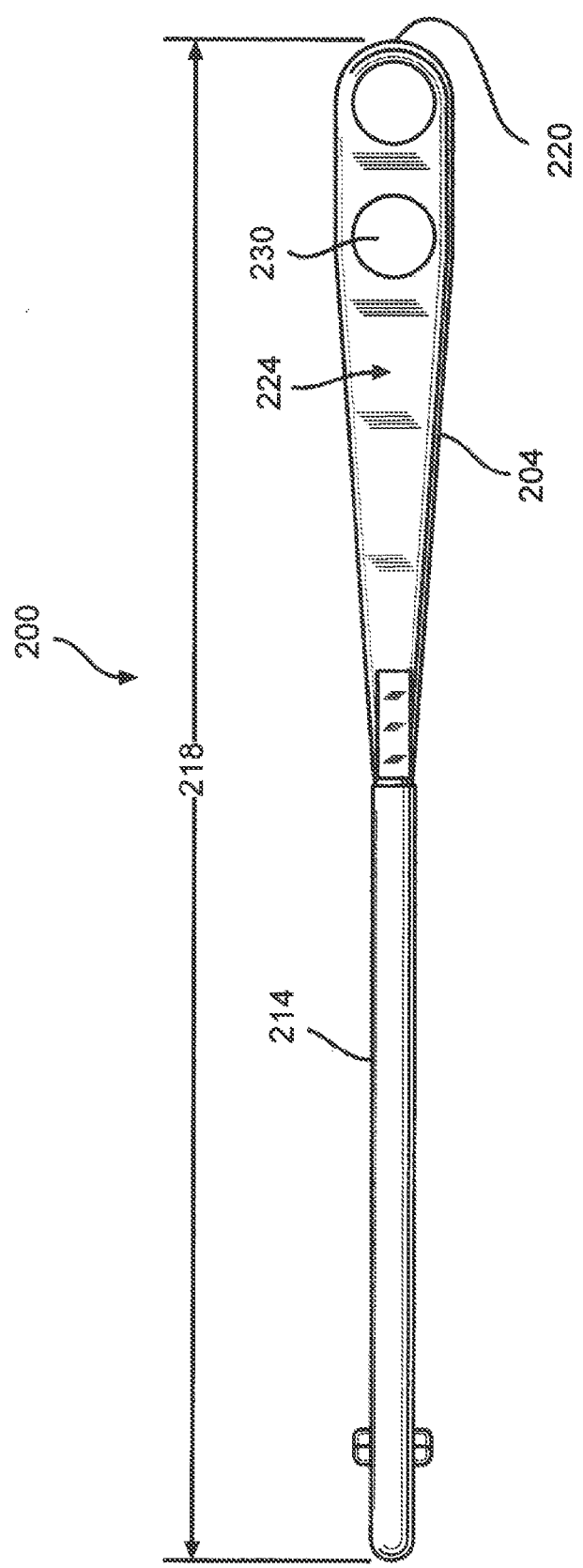
FIG. 8 shows a top view of the posterior acetabular retractor embodiment shown in FIG. 7.
Figure 9:
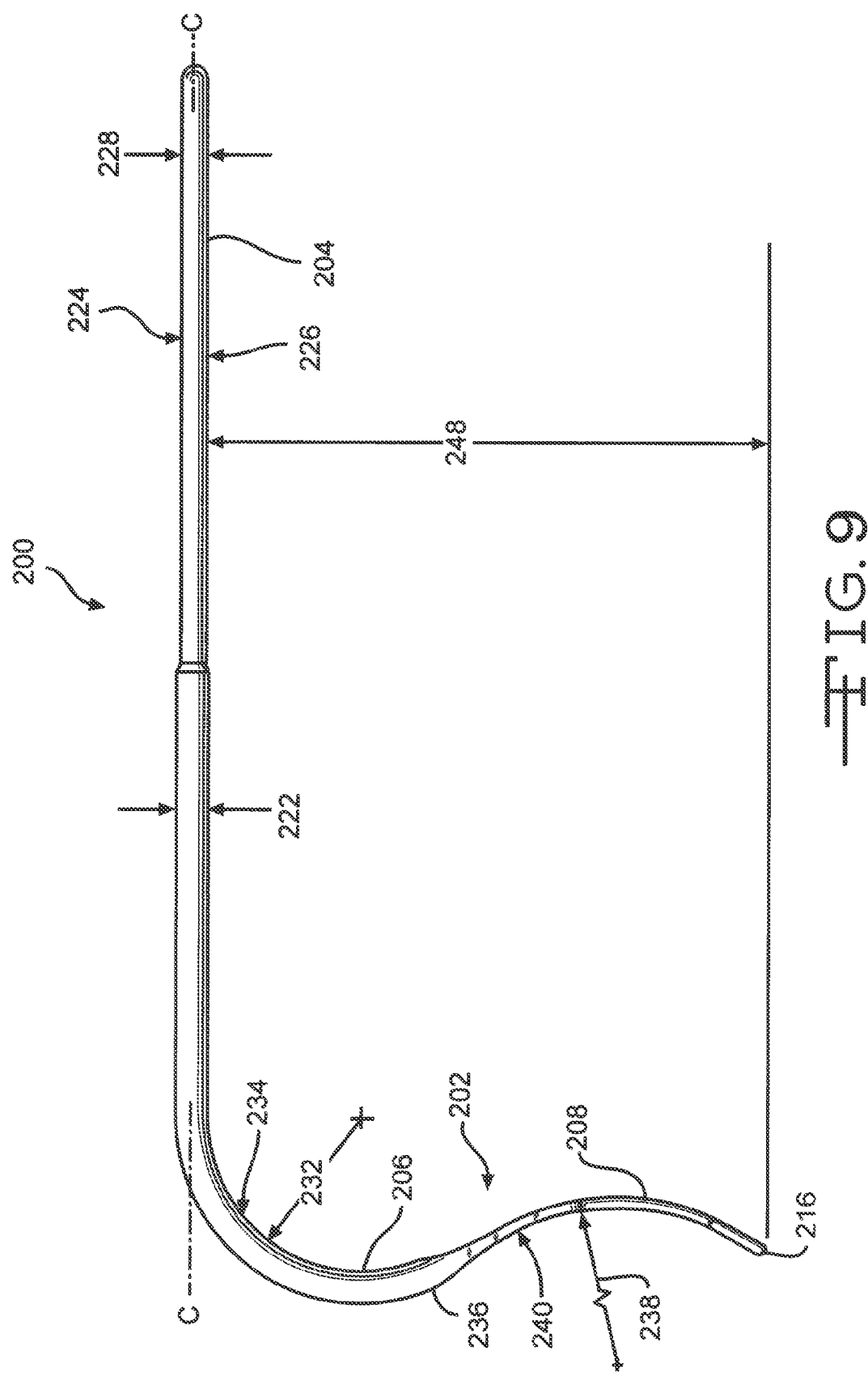
FIG. 9 shows a side view of the posterior acetabular retractor embodiment shown in FIG. 7.

The second bend portion 208 has a second radius of curvature 238. The second radius of curvature 238 is defined by the curved radius that resides along a surface 240 of the bend portion 208 from the apex point 236 to the end of the distal portion 216. It is preferred that the second bend portion 208 has a second radius of curative 238 that ranges from about 2 mm to about 10 mm. The second bend portion 208 generally has a curved cross sectional profile perpendicular to its length, and more preferably, a round cross-sectional profile. A prong 242 preferably extends outwardly and upwardly from an edge 244 of the distal portion 212. As illustrated in FIG. 7, the width 250 of the prong 242 gradually decreases to a pointed end which corresponds to the distal end 216 of the retractor 200.

In a preferred embodiment, the distal portion 212 is of a generally rectangular shape with a distal portion width 246, length 252 and thickness 254. In a preferred embodiment, the width 246 of the distal portion 212 ranges from about 10 mm to about 20 mm, the distal portion length 252 ranges from about 15 mm to about 30 mm and the distal portion thickness 254 ranges from about 1 mm to about 5 mm. As shown in FIG. 7, the prong 242 extends distally from an edge 244 of the distal portion 212. In a preferred embodiment, the prong 242 extends about 2 mm to about 10 mm from the edge 244 of the distal portion 212. Furthermore, the prong 242 may extend upwardly or downwardly from the edge 244 of the distal portion 212. Additionally, a height 248 between the distal end 216 of the retractor 200 to the bottom surface 226 of the handle portion 204 ranges from about 100 mm to about 200 mm.

Alternatively, retractor 200 may be designed without the second bend portion 208, comprising only the first bend portion 206. In this alternative embodiment, the distal portion 212 extends downwardly from horizontal axis CC such that the distal portion is generally about perpendicular to the horizontal axis C-C.

FIGS. 10, 10A, 103, 11, 11A and 12 illustrate embodiments of a retractor 300 generally referred to as an "anterior retractor". As illustrated, retractor 300 has a generally curved shape with a distal portion 302 that extends from a handle portion 304 at a proximal end 308. A wound contact portion 310 extends therebetween.

In a preferred embodiment, the retractor 300 has a bend portion 312 that is defined by a curved surface 314 (FIG. 12) that extends between the distal portion 302 and the handle portion 304. The bend portion 312 further has a radius of curvature 316 that extends from an axis DD that is co-planar with the handle portion 304 to the distal portion 302. In a preferred embodiment, the radius of curvature 316 ranges from about 10 mm to about 50 mm.

Figure 10A:
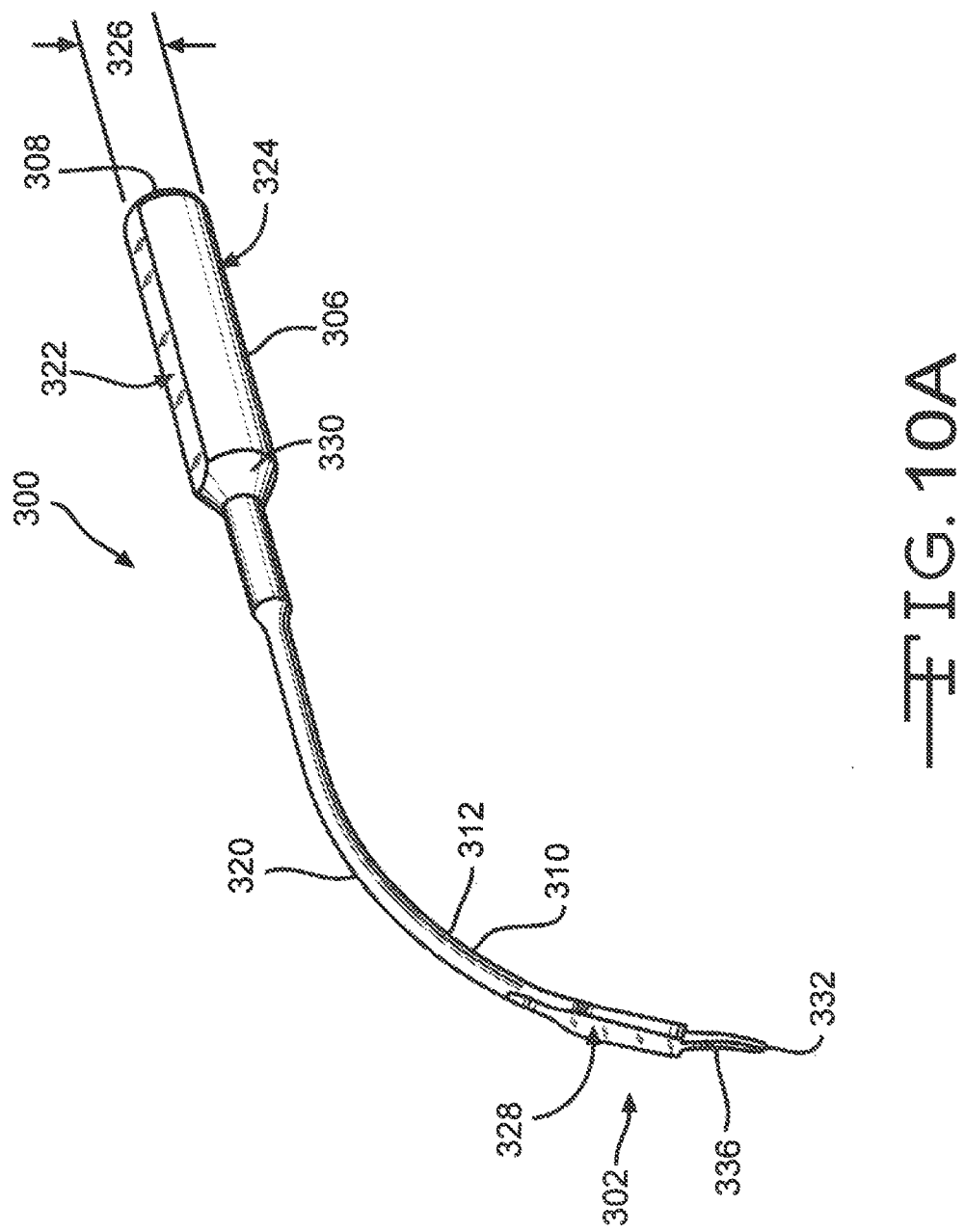
FIG. 10A shows a cross-sectional view of a shaft of the anterior retractor embodiment shown in FIG. 10.

In a preferred embodiment, the retractor 300 has a length 318 that extends between the proximal end 308 and the wound contact portion 310 in a preferred embodiment, the length 318 ranges from about 200 mm to about 300 mm. Residing between the handle portion 304 and the distal end portion 302 is a shaft 320. The shaft 320 generally has a curved cross sectional profile perpendicular to its length, and more preferably, a round cross-sectional profile (FIG. 10A). In a preferred embodiment, a thickness 342 of the shaft 320 is of a diameter that ranges from about 5 mm to about 10 mm.

Similarly to retractors 100 and 200 as previously discussed, the handle portion 304 of retractor 300 resides at the proximal end 308. Like retractors 100 and 200, the handle portion 308 has a generally rectangular cross-section with a generally planar to 322 and bottom surface 324. Alternatively the handle portion 304 may be constructed with a round or oval cross-section. An alternate handle 306 design is shown in FIGS. 103 and 11A. As illustrated, these alternative handle portion embodiments generally have a handle portion thickness 326 that is greater than shown in FIGS. 10 and 12. Furthermore, the alternative handle portion 306 embodiment features a generally frustro-conical handle nose 330. Either handle portion embodiment 304 or 306 may have a handle thickness 326 that can be larger or smaller than the thickness of the shaft 320. An opening 328 may extend through the handle portion 304 from the top surface 322 through the bottom surface 324. The handle portion 304, 306 preferably has a thickness 326 ranging from about 3 mm to about 15 mm. Furthermore, a height 340 extends between the distal end 302 of the retractor 300 and the bottom surface 324 of the handle portion 304. In a preferred embodiment, the height 340 ranges from about 100 mm to about 200 mm.

The distal portion 302 of retractor 300 preferably has a rectangular cross-sectional profile. However, the distal portion 302 may have a curved or round cross-sectional profile.

In a preferred embodiment, the distal portion has a generally planar surface 328 that extends from the wound contact portion 310 to a distal end 332 of the distal portion 302. Preferably, the distal surface 328 has a width 334 that ranges from about 5 mm to about 20 mm. It is also preferred that the distal portion 302 may have a thickness 338 that ranges from about 1 mm to about 5 mm.

Figure 11:
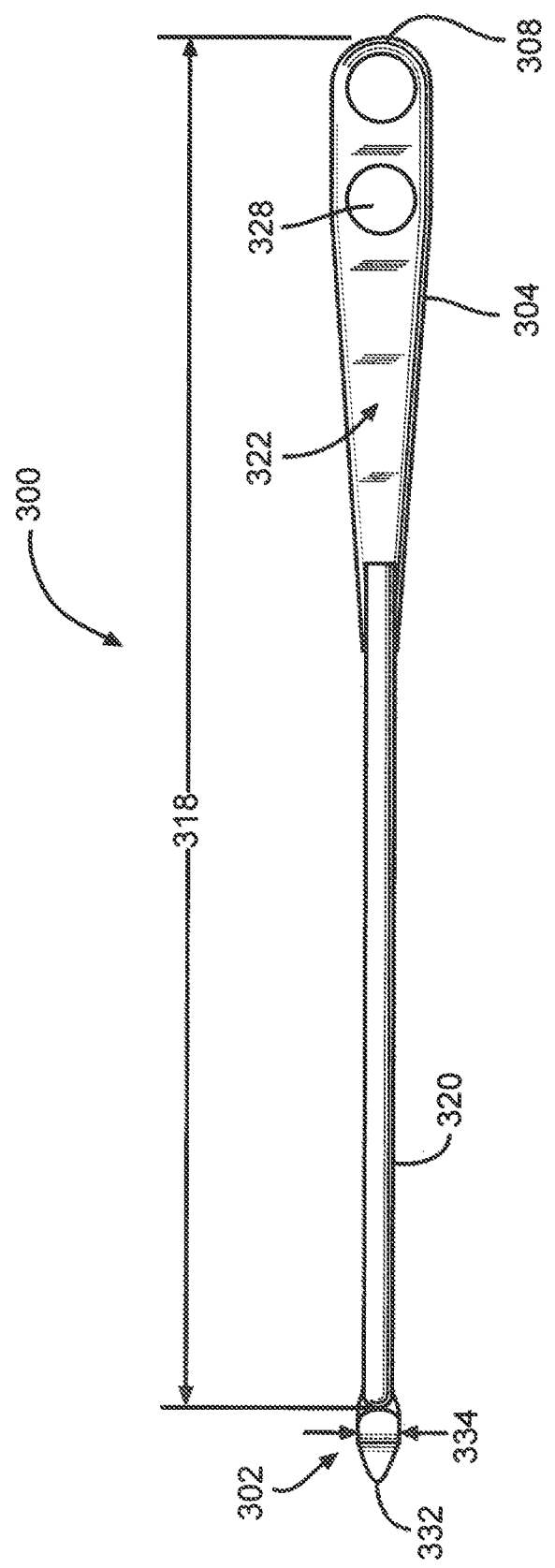
FIG. 11 shows a top view of the anterior retractor embodiment.
Figure 11A:
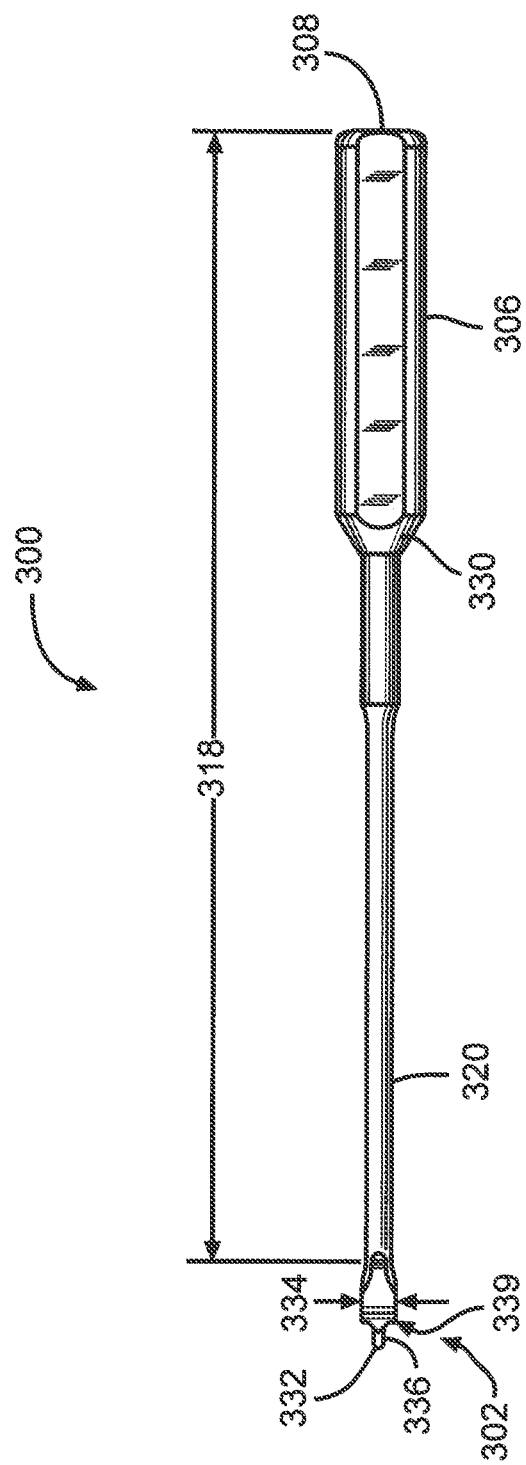
FIG. 11A illustrates a top view of the alternate embodiment of the anterior retractor shown in FIG. 10A.
Figure 12:
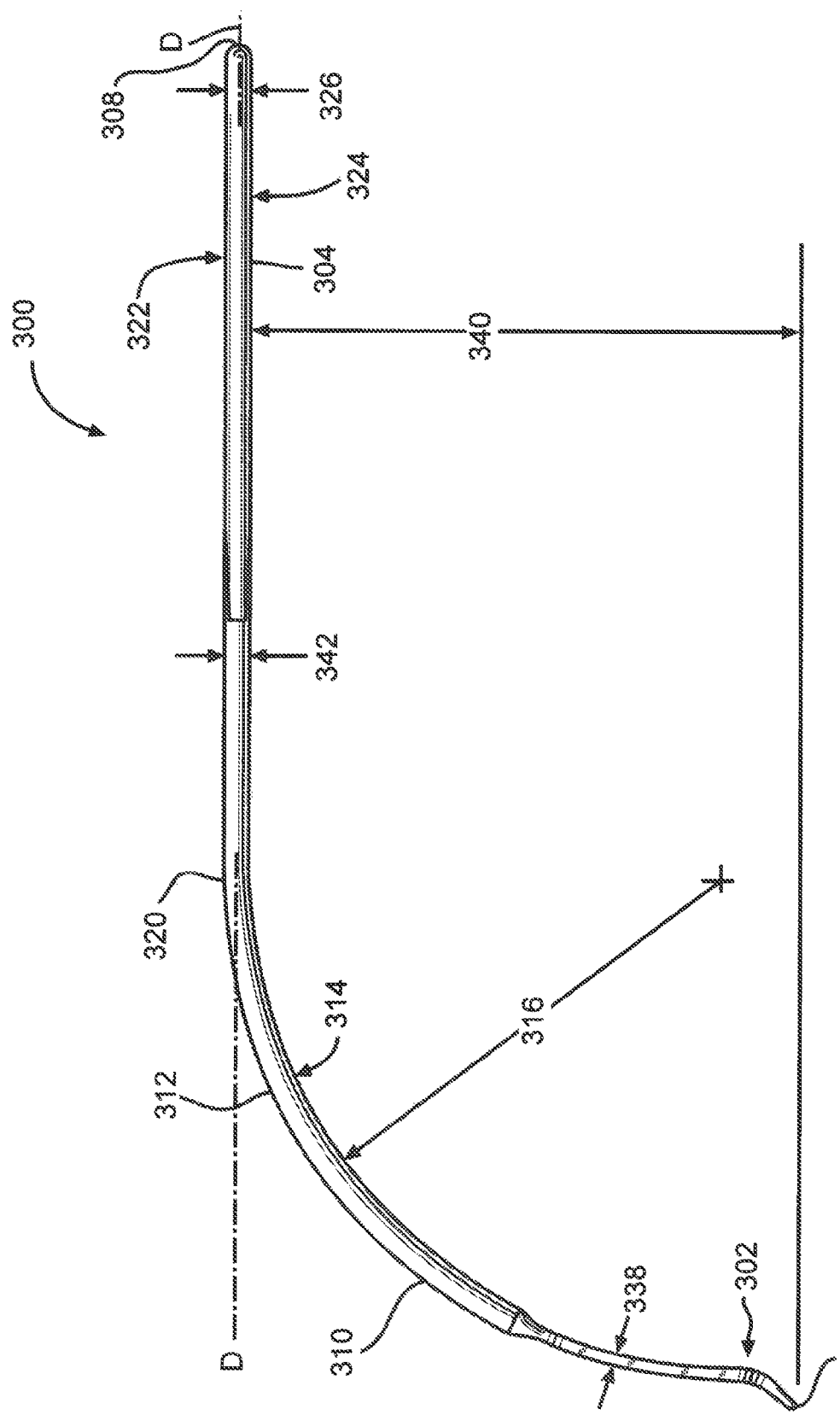
FIG. 12 shows a side view of the anterior retractor shown in FIG. 10.

In the embodiment illustrated in FIGS. 10 and 11, the width 334 of the distal portion 302 gradually narrows to a point at the end 332 of the distal portion 302. This point as illustrated in FIGS. 10 and 11, generally curls upwardly and outwardly from the planar surface 328. However, it is contemplated that this point 332 may also curl downwardly and way from the planar surface 328.

Alternatively, as illustrated in FIGS. 103 and 11A, a prong 336 extends from an edge 339 of the distal portion 302 of the retractor 300. In this alternative embodiment, the width of the prong 336 is substantially and abruptly smaller than the width of the edge 339 of the distal portion 302. The end of the prong 336, i.e., the end 332 of the distal portion 302, may curve upwardly or downwardly away from the plane of the distal portion surface 328.

FIGS. 13, 13A, 14 and 15 illustrate an embodiment of a retractor 400 generally referred to as a "femoral neck retractor". The retractor 400 comprises a handle portion 402, a bend portion 404, a wound contact portion 406, and a distal portion 408.

As illustrated, a shaft 410 extends therebetween the distal end portion 408 and the handle portion 402. In a preferred embodiment, the shaft 410 generally has a curved cross-sectional profile perpendicular to its length, and more preferably, a round cross-sectional profile (FIG. 13A). The shaft 410 preferably has a thickness 412 with a diameter that ranges from about 2 mm to about 20 mm. A length 414 extends from a proximal end 434 to the end of the distal portion 408 of the retractor 400. In a preferred embodiment, the length 414 ranges from about 200 mm to about 400 mm.

Similarly to the retractors 100, 200 and 300 previously discussed, the handle portion 402 of retractor 400 resides at the proximal end 434 of the retractor 400. Like retractors 100, 200 and 300, the handle portion 402 generally embodies a rectangular cross-sectional profile with a generally planar top 436 and bottom surface 438. Alternatively, the handle portion 402 may be constructed with a round or oval cross-section. The handle thickness 440 may be larger or smaller than the thickness of the shaft 410. An opening may extend through the handle portion 402 from the top surface 436 through the bottom surface 438. The handle portion 402 preferably has a thickness 440 ranging from about 3 mm to about 15 mm. Furthermore, a height 432 extends between the distal end portion 408 of the retractor 400 and the bottom surface 438 of the handle portion 402. In a preferred embodiment, the height 432 ranges from about 100 mm to about 200 mm.

Figure 13:
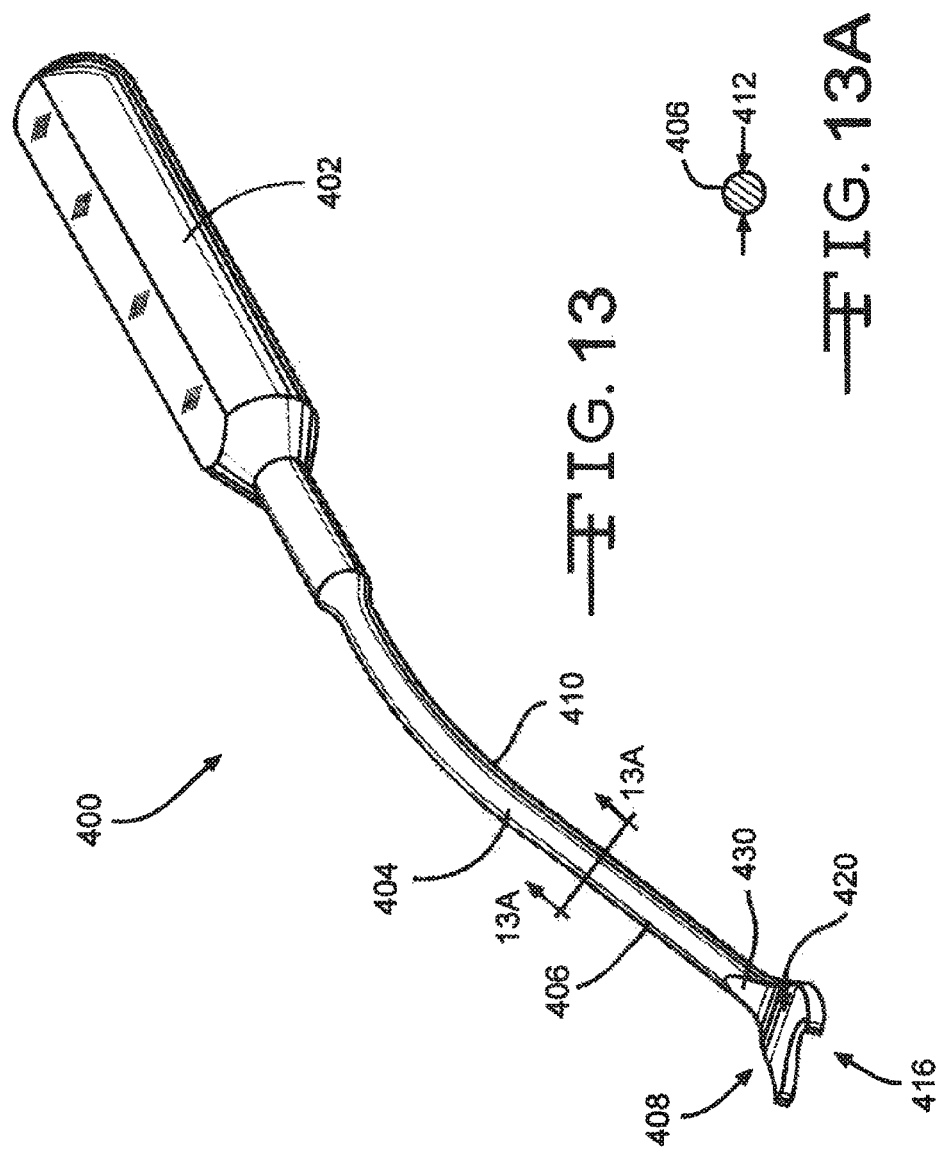
FIG. 13 illustrates a perspective view of an embodiment of a femoral neck retractor.
Figure 14:
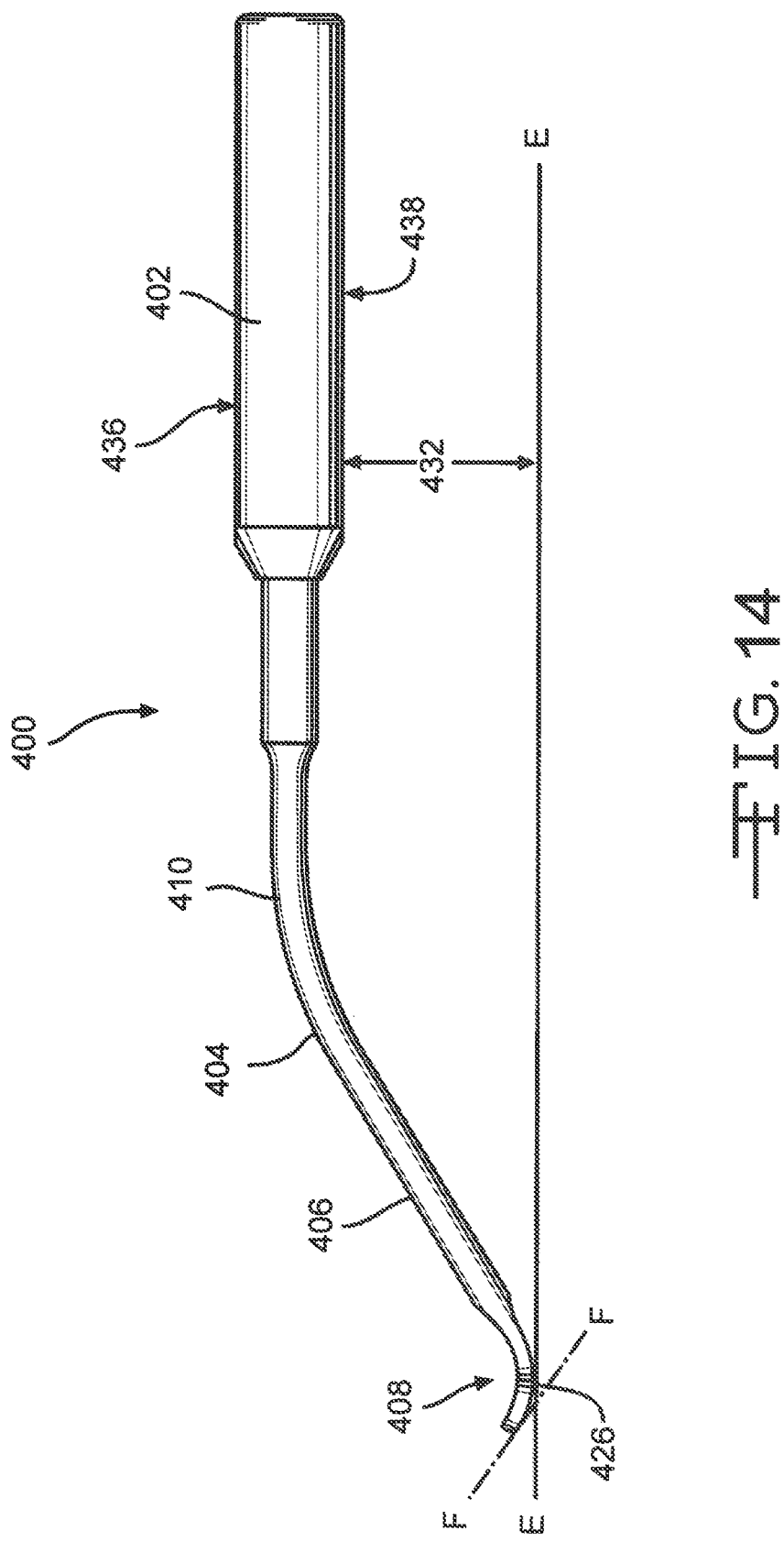
FIG. 14 illustrates a side view of the embodiment of the femoral neck retractor shown in FIG. 13.
Figure 15:
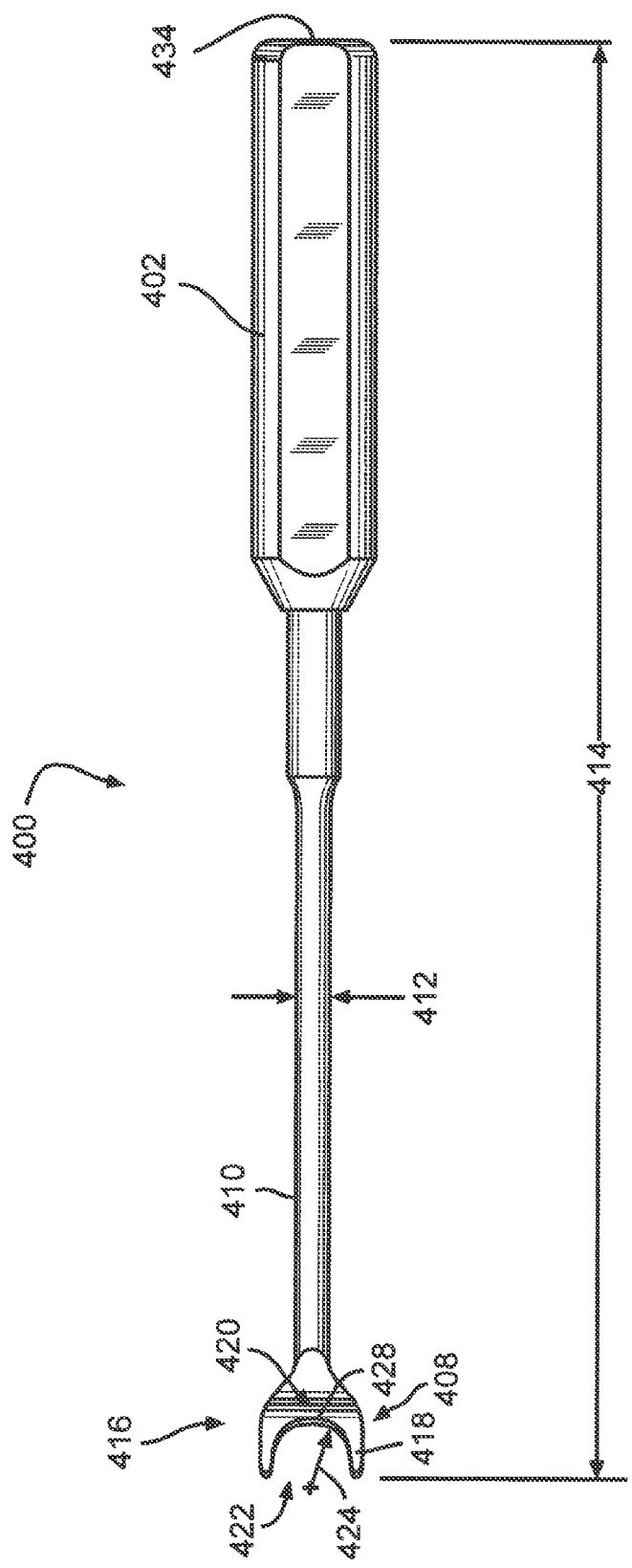
FIG. 15 shows a top view of the femoral neck retractor shown in FIG. 13.
Figure 16:
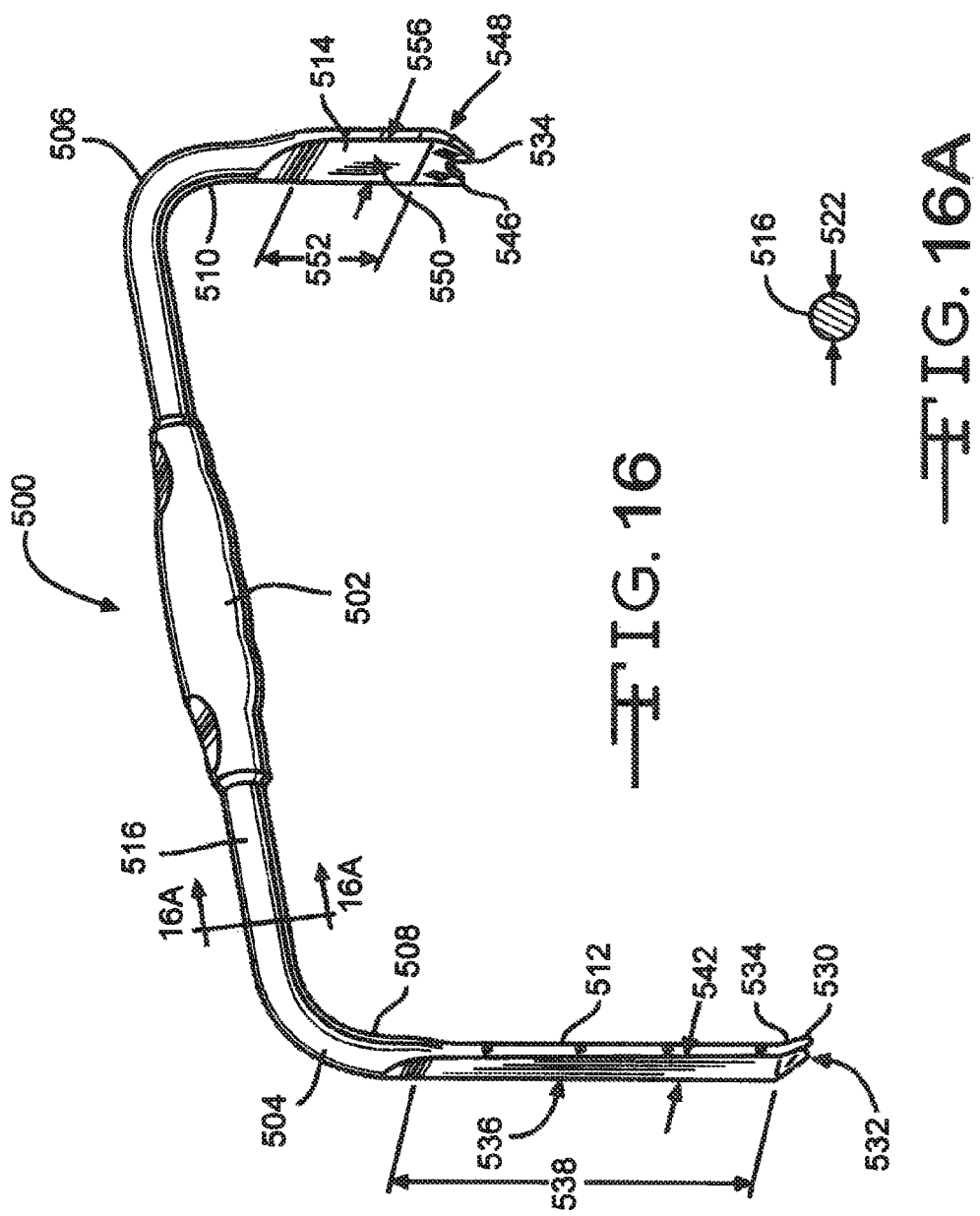
FIG. 16 illustrates a perspective view of an embodiment of a double ended retractor.

In an embodiment illustrated in FIGS. 13, 14 and 15, the distal end portion 408 comprises a claw portion 416. More preferably, the claw portion 416 comprises at least one prong 418. These prongs 418 extend distally from a surface 420 of the claw 416. An inlet 422 residing between the two prongs 418 provides a space that separates the prongs 418. A claw radius of curvature 424 defines the opening of the inlet 422 between the prongs 418. In a preferred embodiment, the radius of curvature 424 ranges from about 5 mm to about 25 mm.

It is further preferred that the claw portion 416 is inclined about a bottom claw point 426. An incline angle 442 is defined as the angle between a horizontal axis E-E that intersects and extends parallel to the bottom point 426 and imaginary line F-F that is tangent of a bottom surface 444 of the claw 416. In a preferred embodiment, the claw 416 has an incline angle 442 ranging from about 5° to about 25°.

It is additionally preferred that the claw surface 420 extends from an inlet apex 428 to a portion 430 between the proximal end of the claw portion 416 and the distal end of the shaft 410. Furthermore, the curved surface 420 of the claw 416 is preferably depressed inwards towards the body of the claw 416, thereby creating an inclined or "wedge like" surface 420 that resides between the end of the prongs 418 and a proximal end of the distal portion 408. This inclined or "wedge like" surface 420 of the claw 416 assists and provides additional engagement of the femoral neck retractor 400. The retractor 400 further has a shaft thickness 412 with a diameter ranging from about 5 mm to about 10 mm.

FIGS. 16, 16A, 17 and 18 illustrate embodiments of a retractor 530 generally referred to as a "double ended retractor". The retractor 500 comprises a handle portion 502, a first bend portion 504, a second bend portion 506, a first wound contact portion 508, a second wound contact portion 510, a first distal end portion 512, and a second distal end portion 514. A surgeon can therefore use one or both of the first and second distal end portions 512, 514 during an orthopedic surgical procedure.

As illustrated, the handle portion 502 is located between the first and second distal end portions 512, 514. A shaft 516 extends from a left side 518 and right side 520 of the handle portion 502. The shaft 516 connects the handle portion 502 to the respective distal end portions 512, 514. In a preferred embodiment, the shaft 516 generally has a curved cross-sectional profile perpendicular to its length, and more preferably, a round cross-sectional profile (FIG. 16A). The shaft 516 preferably has a thickness 522 with a diameter that ranges from about 5 mm to about 10 mm. Furthermore, the overall length 528 of retractor 500 extending from the first bend portion 504 to the second bend portion 506, preferably ranges from about 200 mm to about 400 mm.

Residing between the handle portion 502 and the first distal end portion 512 is the first bend portion 504. The first wound contact portion 508 resides therebetween the first distal end portion 512 and the first bend portion 504.

The first bend portion 504 is defined by a first bend angle 524 that generally measures about 90°. The first bend angle 524 is measured between horizontal axis GG, co-axial to the handle portion 502, and perpendicular axis H-H. Although a 90° first bend angle 524 is preferred, the angle 524 may range from about 70° to about 130°.

Additionally, residing between the handle portion 502 and the second distal end portion 514 is a second bend portion 506. A second wound contact portion 510 resides therebetween the second distal end portion 514 and the second bend portion 506.

The second bend portion 506 is defined by a second bend angle 526 that generally measures about 90°. The second bend angle 526 is measured between horizontal axis G-G, co-axial to the handle portion 502, and perpendicular axis I-I. Although a 90° second bend angle 526 is preferred, the angle 526 may range from about 70° to about 130° Furthermore, the first and second angles 524, 526 may or may not be equal.

Figure 17:
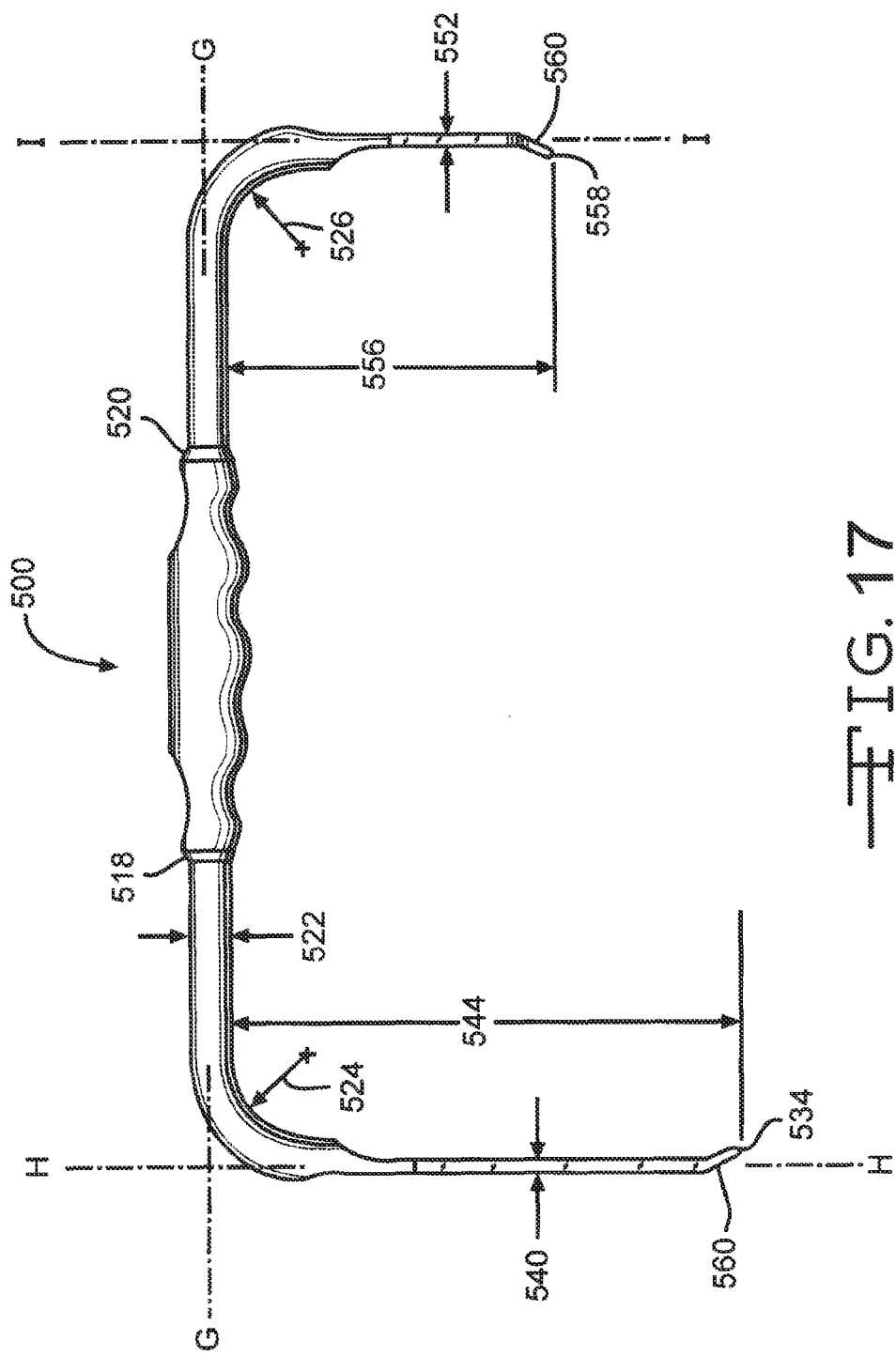
FIG. 17 shows a side view of the double ended retractor shown in FIG. 16.
Figure 18:
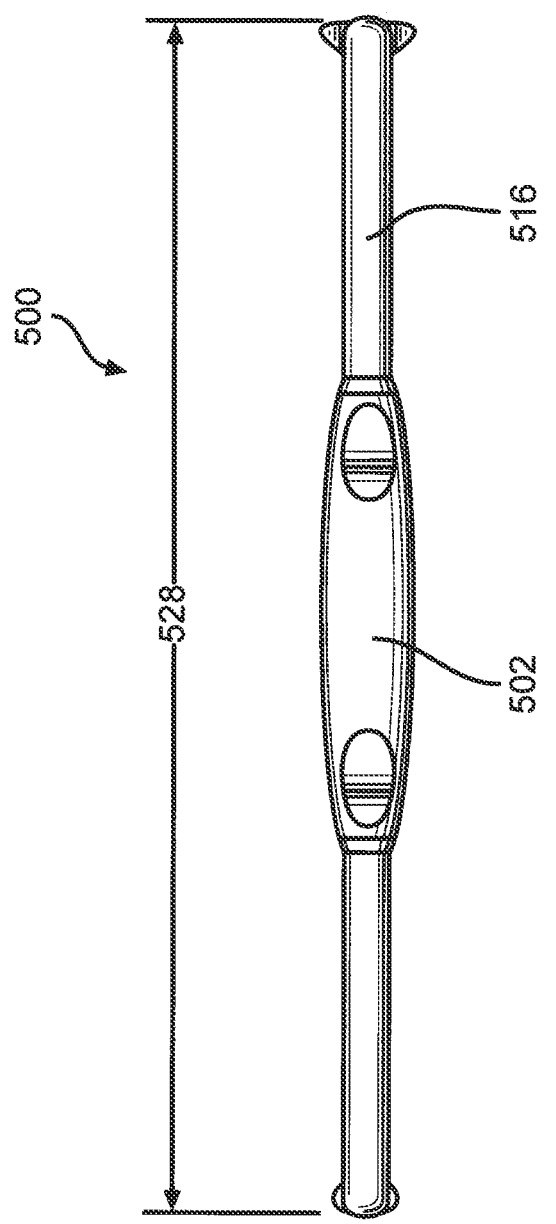
FIG. 18 shows a top view of the double ended retractor shown in FIG. 16.

The first distal end portion 512 extends from the distal end of the first wound portion 508 to a distal end 530 of the first distal end portion 512. The first distal end portion 512 preferably has a generally rectangular cross-section. However, the distal portion 512 may have a curved or round cross-sectional profile. A first claw portion 532 preferably comprising at least one prong 534 extends to the end 530 of the first distal end portion 512. The claw portion may or may not be positioned such that it curves inwardly and outwardly from perpendicular axis H-H as shown in FIG. 17.

Additionally, it is preferred that the first distal end portion 512 comprises a planar first distal end portion surface 536. Although this surface 536 may not necessarily be constructed such that it is planar. Instead, it may be designed with a curved surface. This surface 536 enables the user to place the end of the retractor 530 between muscles and/or tissue with increased precision and ease. In a preferred embodiment a length 538 of the first distal end portion surface 538 is from about 20 mm to about 60 mm. Furthermore, the first distal end portion 512 has a thickness 540 that ranges from about 2 mm to about 10 mm and a first distal end width 542 that ranges from about 5 mm to about 30 mm. A first distal end portion height 544 preferably extends from the distal end 530 of the first distal end portion 512 to the first bend portion 504. In a preferred embodiment, the first distal end portion height 544 ranges from about 50 mm to about 150 mm.

The second distal end portion 514 extends from the distal end of the second wound portion 510 to a distal end 546 of the second distal end portion 514. The second distal end portion 514 preferably has a generally rectangular cross-section. However, the distal portion 514 may have a curved or round cross-sectional profile. A second claw portion 548 preferably comprising at least one prong 534 extends to the end 545 of the second distal end portion 514. The second claw portion 548 may or may not be positioned such that it curves inwardly from perpendicular axis I-I as shown in FIG. 17. Alternatively, the second claw portion 548 may be positioned outwardly from perpendicular axis I-I.

It is further preferred that the second distal end portion 514 comprise a planar second distal end portion surface 550. However, this surface 550 may not necessarily be constructed such that it is planar. Instead, it may be designed with a curved surface. This surface 550 enables the user to place the end of the retractor 546 between muscles and/or tissue with increased precision and ease.

In a preferred embodiment, the length 552 of the second distal end portion surface 550 ranges from about 10 mm to about 30 mm. Furthermore, the second distal end portion 514 has a thickness 554 from about 2 mm to about 10 mm and a second claw width 556 that preferably ranges from about 2 mm to about 20 mm. A second distal end portion height 558 extends from the distal end 546 of the second distal end portion 514 to the second bend portion 506. In a preferred embodiment, the second distal end portion height 558 ranges from about 20 mm to about 80 mm.

Advantageously, the curved cross-section of the retractors 100, 200, 300, 400 and 500 inhibit necrosis of the tissue of the incision, that contacts the wound contact portions 106, 210, 310, 406, 508, 510 thereby allowing a surgeon to perform the surgical procedure without traumatizing the tissue. This helps reduce the length of the surgical procedure and retain the tissue of the tissue generally intact. Additionally, the curved cross-sectional profile and reduced cross-sectional dimensions of the retractor 500 allows the retractor or multiple retractors to be placed in a variety of positions within the incision while allowing the insertion of other surgical tools (e.g. reamer) through the access space defined through the incision.

Additionally, unlike conventional retractors, which have a generally flat and rectangular cross-sectional profile, the curved cross-sectional profile and reduced cross-sectional dimensions of the retractors 100, 200, 300, 400 and 500 helps prevent contact with the reamer when the latter is inserted through the access space defined by the incision and operated to ream the acetabulum. Though conventional retractors with smaller widths have been tried, the reduction in width generally resulted in a decreased retractor strength that can lead to damage of the retractor. In contrast, the retractors 100, 200, 300, 400 and 500 described above inhibit such jamming with the reamer while retaining sufficient strength to inhibit breaking of the retractors 100, 200, 300, 400 and 500 during the surgical procedure.

In one embodiment, one or more of at least one of the retractors 100, 200, 300, 400 and 500 of FIGS. 4-18 can be provided as part of a kit. However, in another embodiment, fewer or more retractors can be provided as part of the kit, each retractor having a different shape, with each retractor 100, 200, 300, 400 and 500 having a generally round cross-sectional profile or generally oval cross-sectional profile at the location where the retractor engages the tissue defined by the incision. The retractors 100, 200, 300, 400 and 500 can be made of any suitable known material for use in surgical procedures. Preferred examples of such materials include, but are not limited to, stainless steel, MP35N, aluminum, as well as polymeric and ceramic materials.

Of course, the forgoing description is that of certain features, aspects and advantages of the present invention, to which various changes and modifications can be made without departing from the spirit and scope of the present invention. Moreover, the retractors need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of these specific features and aspects of embodiments may be made and still fall within the scope of the invention. Accordingly, it should be understood that various features and aspects of embodiments may be made and still fall within the scope of the invention. Accordingly, it should be understood that various features and aspects of the disclosed embodiments can be combined with or substituted for one another in order to form varying modes of the discussed retractor system and kit. Additionally, one of ordinary skill in the art will recognize that the retractor embodiments described herein are not limited for use in hip replacement surgeries, or for use in orthopedic surgical procedures, but can be used in other surgical procedures (e.g., abdominal or spinal).

What is claimed is:

1. A retractor for use in surgery, the retractor comprising:
   a) a handle configured to be held by a user;
   b) a wound contact plate comprising spaced apart front and back plate faces providing a plate thickness extending to first and second plate edges; and
   c) a shaft comprising a shaft length extending from a proximal shaft portion to a distal shaft portion, wherein the proximal shaft portion is connected to the handle and the distal shaft portion is rigidly connected to the wound contact plate,
   d) wherein the distal shaft portion has:
      i) a round cross-section perpendicular to the shaft length with a diameter of the round cross-section being less than a maximum width of the wound contact plate measured from the first plate edge to the second plate edge; and ii) a first radius of curvature curving proximally along an imaginary plane away from the proximal shaft portion, and iii) wherein the imaginary plane bisects at least the distal shaft portion and the wound contact plate and is a plane of symmetry, and e) wherein the wound contact plate has a second radius of curvature curving along the imaginary plane away from and in an opposite direction with respect to the first radius of curvature of the distal shaft portion with the first radius of curvature meeting the second radius of curvature at an inflection point, and f) wherein the round cross-section of the distal shaft portion ends at the inflection point where the first radius of curvature meets the second radius of curvature and where the distal shaft portion meets the wound contact plate.

2. The retractor of claim 1, wherein the round cross-section of at least the distal shaft portion has a diameter that ranges from 5 mm to 10 mm.

3. The retractor of claim 1, wherein the shaft has the round cross-section extending from the proximal shaft portion connected to the handle to the distal shaft portion connected to the wound contact plate.

4. The retractor of claim 1, wherein the handle has an opening extending through a handle thickness.

5. The retractor of claim 1, wherein the handle comprises at least one of a planar top surface or a planer bottom surface.

6. The retractor of claim 1, wherein a prong extends distally from the wound contact plate.

7. The retractor of claim 6, wherein the prong extends either away from or towards the proximal shaft portion.

8. The retractor of claim 6, wherein the prong has a length and a width and wherein the prong width decreases along the prong length to a pointed distal end of the prong.

9. The retractor of claim 6, wherein the prong extending distally from the wound contact plate has a length ranging from 2 mm to 10 mm.

10. The retractor of claim 1, wherein the first radius of curvature of the distal shaft portion ranges from 5 mm to 25 mm.

11. The retractor of claim 1, wherein the retractor is of a material selected from the group consisting of a metal, a polymer, and a ceramic.

12. The retractor of claim 1, wherein the wound contact plate has a width between the first and second plate edges that ranges from 10 mm to 20 mm, a length that ranges from 15 mm to 30 mm, and the thickness between the front and back plate faces ranges from 1 mm to 5 mm.

13. A retractor for use in surgery, the retractor comprising:
a) a handle configured to be held by a user;
b) a wound contact plate comprising spaced apart front and back plate faces providing a plate thickness extending to first and second plate edges;
c) a prong that extends distally from the wound contact plate; and
d) a shaft comprising a shaft length extending from a proximal shaft portion to a distal shaft portion, wherein the proximal shaft portion is connected to the handle and the distal shaft portion is rigidly connected to the wound contact plate,
e) wherein the distal shaft portion has:

i) a round cross-section perpendicular to the shaft length with a diameter of the round cross-section being less than a maximum width of the wound contact plate measured from the first plate edge to the second plate edge; and ii) a first radius of curvature curving proximally along an imaginary plane away from the proximal shaft portion, and iii) wherein the imaginary plane bisects at least the distal shaft portion, the wound contact plate and the prong, and wherein the imaginary plane is a plane of symmetry, and f) wherein the wound contact plate and the prong have a second radius of curvature curving along the imaginary plane away from and in an opposite direction with respect to the first radius of curvature of the distal shaft portion with the first radius of curvature meeting the second radius of curvature at an inflection point, and g) wherein the round cross-section of the distal shaft portion ends at the inflection point where the first radius of curvature meets the second radius of curvature and where the distal shaft portion meets the wound contact plate.

14. The retractor of claim 13, wherein the prong extends along the second radius of curvature.

15. The retractor of claim 13, wherein the prong extends either away from or towards the proximal shaft portion.

16. The retractor of claim 13, wherein the prong has a length and a width and wherein the prong width decreases along the prong length to a pointed distal end residing on the imaginary bisecting plane.

17. The retractor of claim 13, wherein the prong extending distally from the wound contact plate has a length ranging from 2 mm to 10 mm.

18. The retractor of claim 13, wherein the first radius of curvature of the distal shaft portion ranges from 5 mm to 25 mm.

19. The retractor of claim 13, wherein the second radius of curvature of the wound contact plate ranges from 2 mm to 10 mm.

20. The retractor of claim 13, wherein the retractor is composed of a material selected from the group consisting of a metal, a polymer, and a ceramic.

21. The retractor of claim 13, wherein the wound contact plate has a width between the first and second plate edges that ranges from 10 mm to 20 mm, a length that ranges from 15 mm to 30 mm, and the thickness between the front and back plate faces that ranges from 1 mm to 5 mm.

22. The retractor of claim 13, wherein the round cross-section of at least the distal shaft portion has a diameter that ranges from 5 mm to 10 mm.

23. The retractor of claim 13, wherein the shaft has a round cross-section extending from the proximal shaft portion connected to the handle to the distal shaft portion connected to the wound contact plate.

24. The retractor of claim 13, wherein the handle has an opening extending through a handle thickness.

25. The retractor of claim 13, wherein the handle comprises at least one of a planar top surface or a planer bottom surface.

26. A retractor for use in surgery, the retractor comprising:
a) a handle configured to be held by a user;
b) a wound contact plate comprising spaced apart front and back plate faces providing a plate thickness extending to first and second plate edges; and
c) a shaft comprising a shaft length extending from a proximal shaft portion to a distal shaft portion, wherein the proximal shaft portion is connected to the handle and the distal shaft portion is rigidly connected to the wound contact plate, d) wherein the distal shaft portion has:
   i) a round cross-section perpendicular to the shaft length; and
   ii) a first radius of curvature curving proximally along an imaginary plane away from the proximal shaft portion, and
   iii) wherein the imaginary plane bisects at least the distal shaft portion and the wound contact plate and is a plane of symmetry, and e) wherein the wound contact plate has a second radius of curvature curving along the imaginary plane away from and in an opposite direction with respect to the first radius of curvature of the distal shaft portion with the first radius of curvature meeting the second radius of curvature at an inflection point, and f) wherein the round cross-section of the distal shaft portion ends at the inflection point where the first radius of curvature meets the second radius of curvature and where the distal shaft portion meets the wound contact plate.

27. A retractor for use in surgery, the retractor comprising:

a) a handle configured to be held by a user, wherein the handle extends along a longitudinal axis;

b) a shaft comprising a shaft length extending from a proximal shaft portion to a distal shaft portion, wherein the proximal shaft portion is connected to the handle; and c) a wound contact plate rigidly connected to the distal shaft portion and extending distally away from the longitudinal axis of the handle, wherein the wound contact plate comprises spaced apart front and back plate faces providing a plate thickness meeting first and second plate edges, the front and back plate faces and the first and second plate edges extending to a distal plate end, d) wherein the distal shaft portion has:
   i) a round cross-section perpendicular to the shaft length with a diameter of the round cross-section being less than a maximum width of the wound contact plate measured from the first plate edge to the second plate edge; and
   ii) a first radius of curvature curving distally proximally along an imaginary plane away from the proximal shaft portion, and
   iii) wherein the imaginary plane bisects at least the distal shaft portion and the wound contact plate and is a plane of symmetry, and e) wherein the wound contact plate has a second radius of curvature curving along the imaginary plane away from and in an opposite direction with respect to the first radius of curvature of the distal shaft portion with the first radius of curvature meeting the second radius of curvature at an inflection point, and f) wherein the round cross-section of the distal shaft portion ends at the inflection point where the first radius of curvature meets the second radius of curvature and where the distal shaft portion meets the wound contact plate, and g) wherein a distance from a first imaginary line extending along the handle to a parallel second imaginary line intersecting the distal plate end ranges from 100 mm to 200 mm.

* * * * *